United States Patent
Yuan et al.

(10) Patent No.: US 12,060,384 B2
(45) Date of Patent: Aug. 13, 2024

(54) SYNTHESIS OF 1,2,5-TRI-O-BENZOYL-3-DIBENZYLAMINO-3-DEOXYRIBOSE AS INTERMEDIATE FOR PRODUCING 3'-AMINO-3'-DEOXYADENOSINE AND 3'-AMINO-3'-DEOXYGUANOSINE AND THE PROTECTED DERIVATIVES THEREOF

(71) Applicant: BRISTOL-MYERS SQUIBB COMPANY, Princeton, NJ (US)

(72) Inventors: Changxia Yuan, Warren, NJ (US); Michael Anthony Schmidt, Cranbury, NJ (US); Adrian Ortiz, Oak Park, CA (US); Amanda J. Rogers, Asbury, NJ (US); Jason J. Zhu, East Brunswick, NJ (US); Zhongmin Xu, Princeton, NJ (US); Miao Yu, Malvern, PA (US); Eric M. Simmons, East Brunswick, NJ (US); Shulin Wu, Plainsboro, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 467 days.

(21) Appl. No.: 17/428,548

(22) PCT Filed: Feb. 5, 2020

(86) PCT No.: PCT/US2020/016694
§ 371 (c)(1),
(2) Date: Aug. 4, 2021

(87) PCT Pub. No.: WO2020/163415
PCT Pub. Date: Aug. 13, 2020

(65) Prior Publication Data
US 2023/0357306 A1 Nov. 9, 2023

Related U.S. Application Data

(60) Provisional application No. 62/801,251, filed on Feb. 5, 2019.

(51) Int. Cl.
C07H 19/167 (2006.01)
C07H 5/06 (2006.01)

(52) U.S. Cl.
CPC ............. *C07H 19/167* (2013.01); *C07H 5/06* (2013.01)

(58) Field of Classification Search
None
See application file for complete search history.

(56) References Cited

U.S. PATENT DOCUMENTS 10,604,542 B2  3/2020  Glick et al.
10,961,270 B2  3/2021  Glick et al.

FOREIGN PATENT DOCUMENTS

WO  2017123669 A1  7/2017

OTHER PUBLICATIONS

Mellal et al., Organic and Biomolecular Chemistry, 2013, vol. 11 No. 36, pp. 6161-6169. (Year: 2013).*
Beom-Tae Kim, et al., "A Convenient and Versatile Synthesis of 2' (and 3')-Amino (and azido)-2' (and 3')-deoxyadenosine as Diverse Synthetic Precursors of Cyclic Adenosine Diphosphate Ribose (cADPR)", Bull. Korean Chem. Soc. 2004, vol. 25, No. 2, pp. 243-248.
Sanchez-Eleuterio, Alma, et al., "High 1,3-trans Stereoselectivity in Nucleophilic Substitution at the Anomeric Position and β-Fragmentation of the Primary Alkoxyl Radical in 3-Amino-3-deoxy-ribofuranose Derivatives: Application to the Synthesis of 2-epi-(-)-Jaspine B", Journal of Organic Chemistry, 2011, vol. 76, No. 13, pp. 5466-5471.
Zhan-Guo, et al., "Orthogonal Activation of the Reenginecred A3 Adenosine Receptor (Neoceptor) Using Tailored Nucleoside Agonists", J. Med. Chem. 2006, vol. 49, pp. 2689-2702.

* cited by examiner

*Primary Examiner* — Traviss C McIntosh, III
(74) *Attorney, Agent, or Firm* — Elliott Korsen

(57) ABSTRACT

The invention generally relates to improved processes for the preparation of intermediates of a cyclic dinucleotide which is useful as a STING agonist.

23 Claims, No Drawings

SYNTHESIS OF 1,2,5-TRI-O-BENZOYL-3-DIBENZYLAMINO-3-DEOXYRIBOSE AS INTERMEDIATE FOR PRODUCING 3'-AMINO-3'-DEOXYADENOSINE AND 3'-AMINO-3'-DEOXYGUANOSINE AND THE PROTECTED DERIVATIVES THEREOF

CROSS-REFERENCE TO RELATED APPLICATIONS

This application claims the benefit of U.S. Provisional Application No. 62/801,251, filed Feb. 5, 2019, the disclosure of which is incorporated herein by reference in its entirety.

FIELD OF THE INVENTION

The invention generally relates to an improved processes for the preparation of intermediates of a cyclic dinucleotide which is useful as a STING agonist.

BACKGROUND OF THE INVENTION

There is disclosed an improved processes for the preparation of intermediate compounds in the preparation of Compound I of the formula

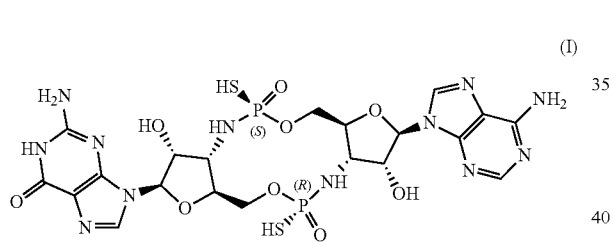

Compound I, compositions comprising Compound I, and an alternate process of preparing Compound I are disclosed in U.S. Ser. No. 15/748,685 filed Jan. 30, 2018, which is assigned to the present assignee and is incorporated herein by reference in its entirety. Compound I may be useful in combination with certain anticancer agents for the treatment of various types of cancer.

SUMMARY OF THE INVENTION

In a first aspect, the invention provides a process for preparing Compound 8 of the formula:

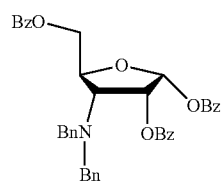

comprising the steps of
a) reacting Compound 1 in a benzoyl protection reaction

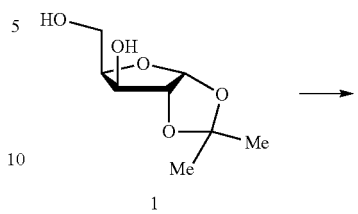

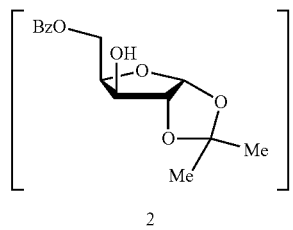

to afford Compound 2;
b) reacting Compound 2 in an oxidation reaction to afford Compound 3;

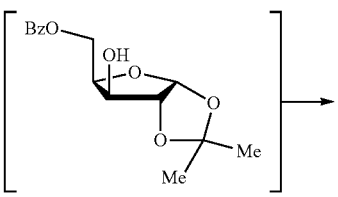

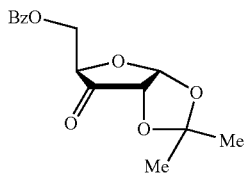

c) which is subsequently reacted in a reductive amination

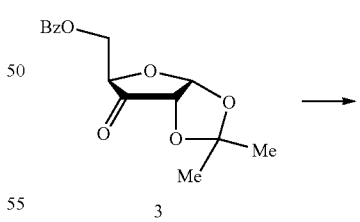

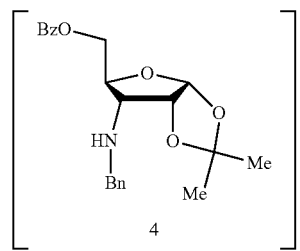

to afford Compound 4;

d) Compound 4 is reacted in a protection step using a benzyl protecting agent and base in a solvent at a temperature of about 70° C. to afford Compound 5 of the formula

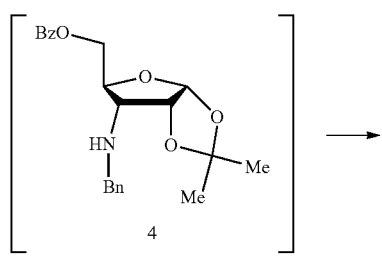

4 e) which is subsequently reacted in a deprotection step with an acid in a common organic solvent to afford Compounds 6 and 7 of the formula

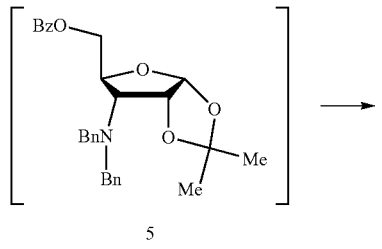

5

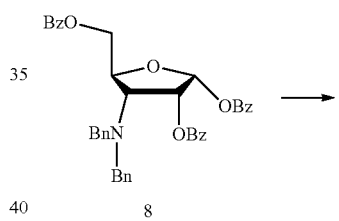

f) and reacting Compounds 6 and 7 with a benzoyl protecting reagent and a base in an organic solvent to afford Compound 8.

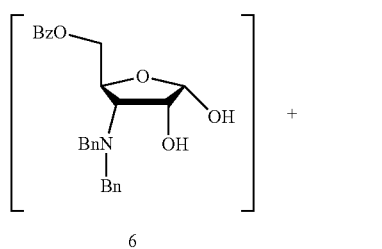

6

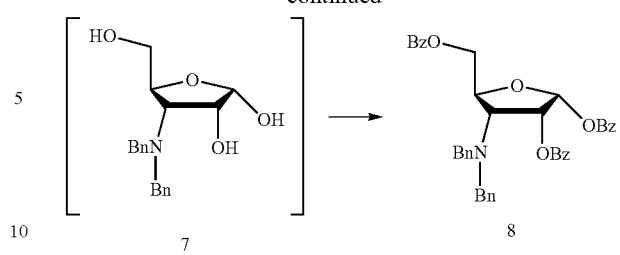

In a second aspect, the invention provides a process for preparing Compound 15 of the formula

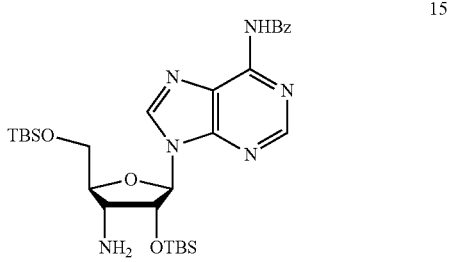

a) which comprises reacting Compound 8 using Vorbrüggen chemistry to afford Compound 9

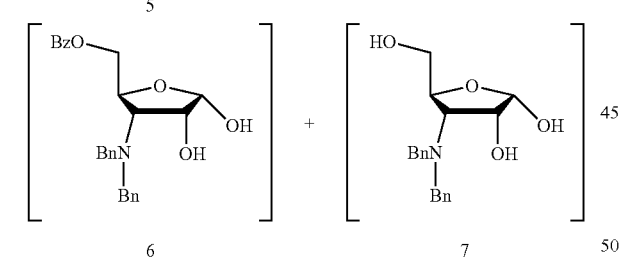

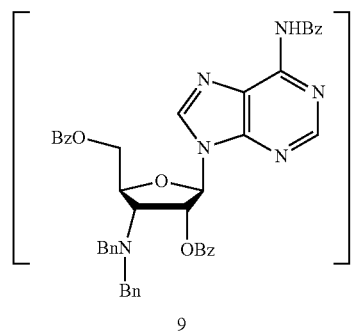

b) which is subsequently deprotected to afford Compound 10 of the formula

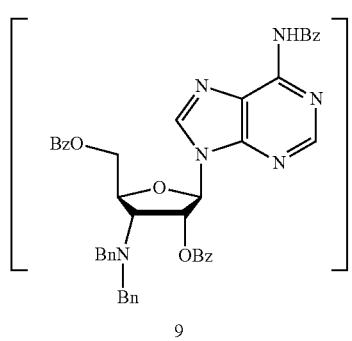
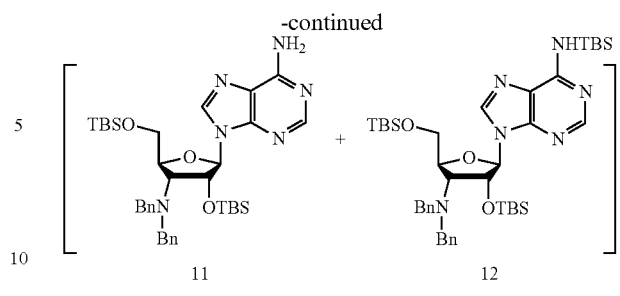
d) which are reacted with a benzoyl protecting reagent to afford Compound 13 of the formula
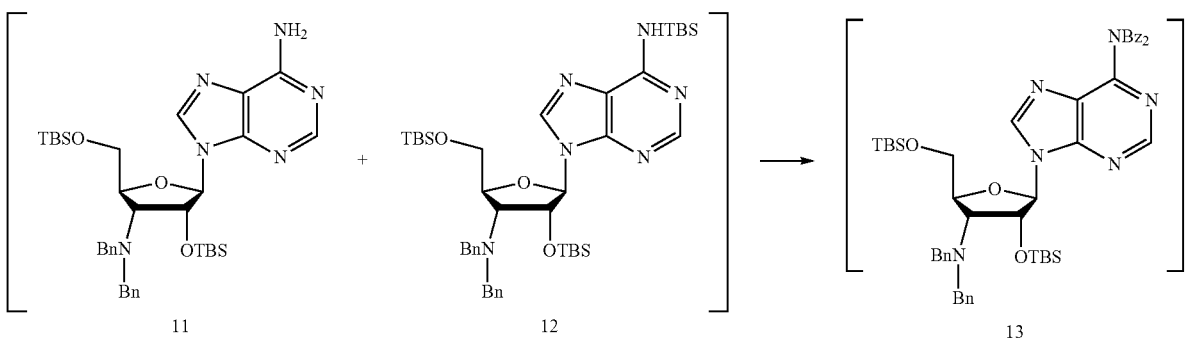
c) which is then subsequently protected to afford Compounds 11 and 12 of the formula
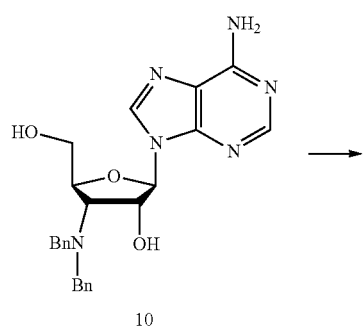
e) Compound 13 is then reacted with ammonia to afford Compound 14 of the formula
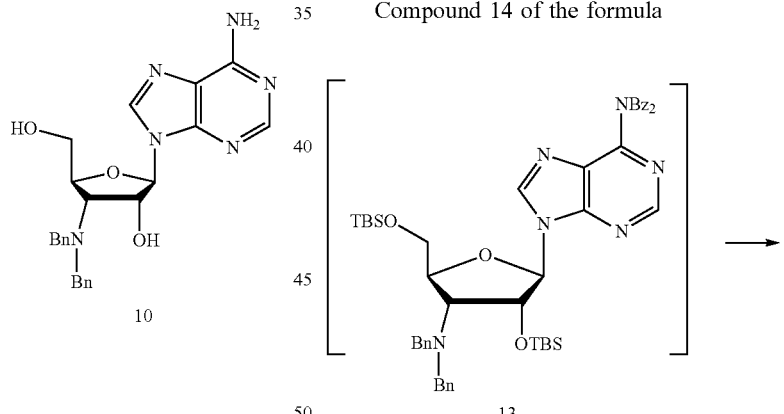
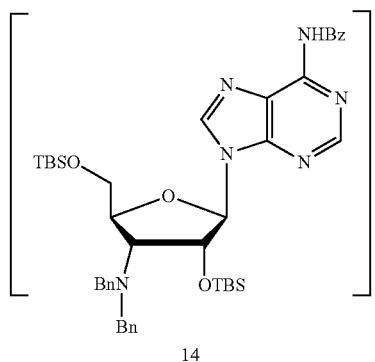

f) which is subsequently hydrogenated to afford intermediate Compound 15 or Compound 15a
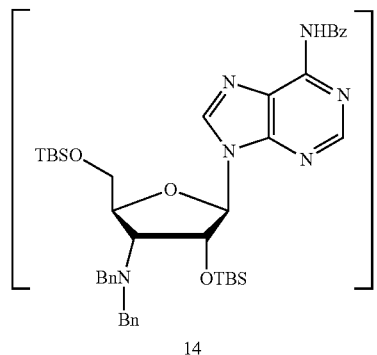
14
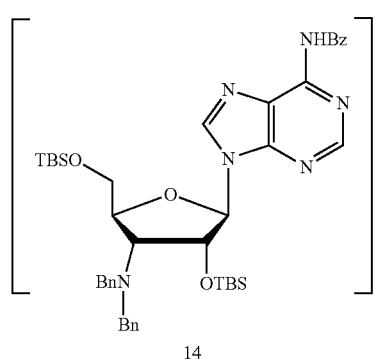
15
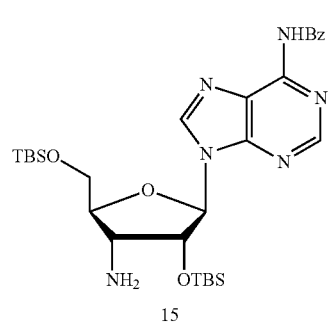
14
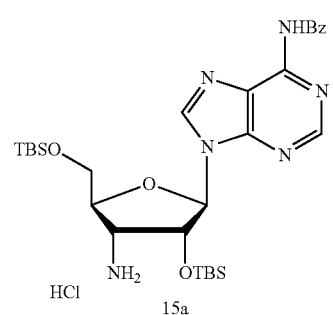
15a
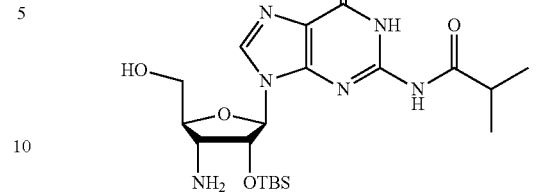
22
which comprises
a) reacting Compound 8 using Vorbrüggen chemistry to afford Compound 16 of the formula
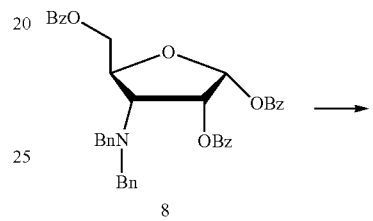
8
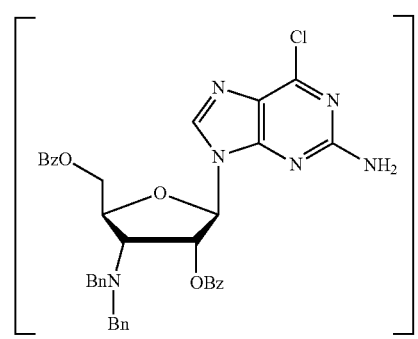
16
b) which is hydrolyzed to afford Compound 17;
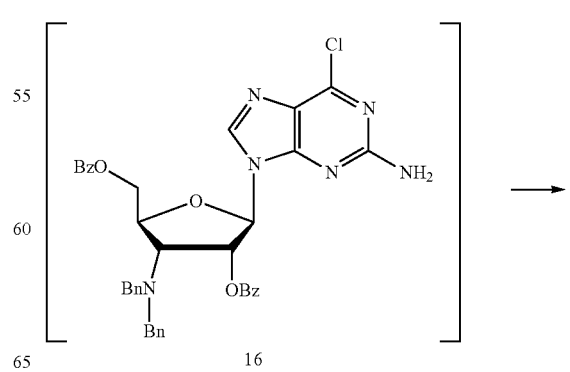
16
In a third aspect, the invention provides a process for preparing Compound 22 of the formula -continued

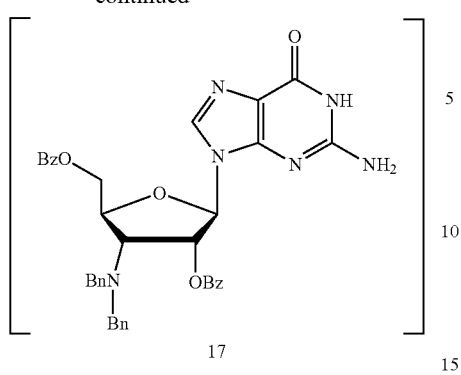

17 c) which is subsequently deprotected to afford Compound 18 of the formula

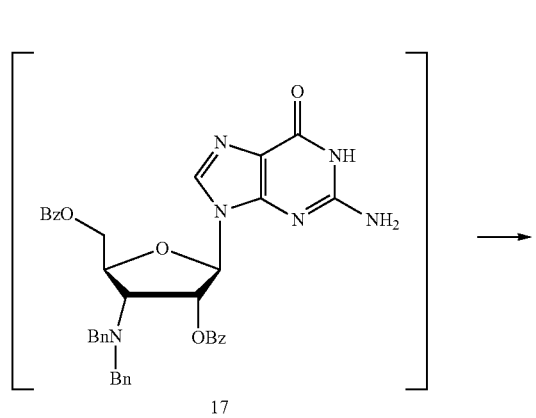

17

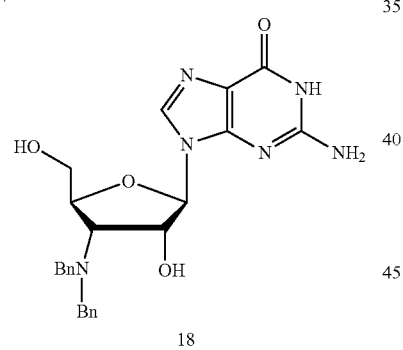

18 d) which is then protected to afford Compound 19 of the formula,

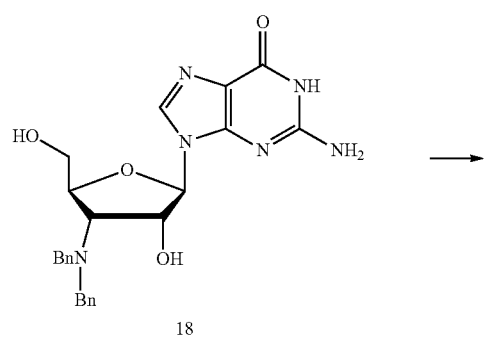

18

-continued

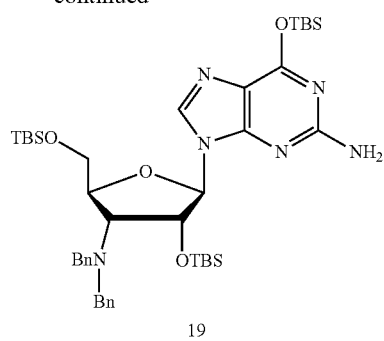

19 e) which is further protected using an isobutyryl containing reagent to afford Compound 20 of the formula,

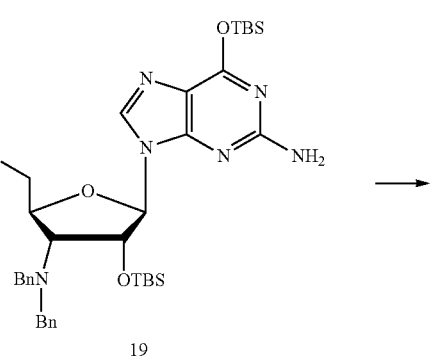

19

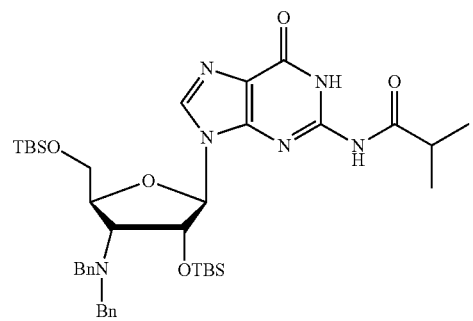

20 or alternatively, Compound 19 is reacted to afford Compound 23 which is further protected using an isobutyryl containing reagent to afford Compound 20

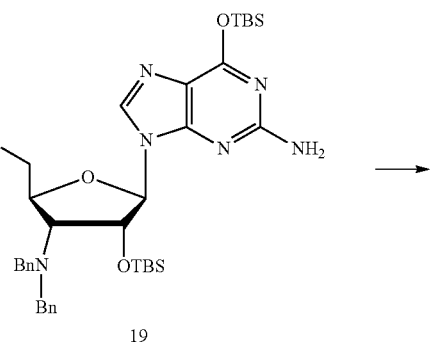

19

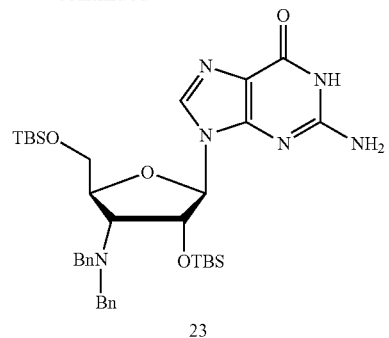

23

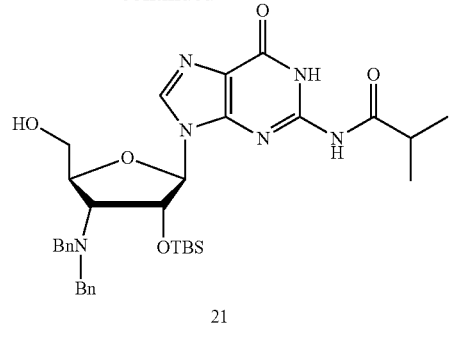

21 g) which is then hydrogenated to afford Compound 22.

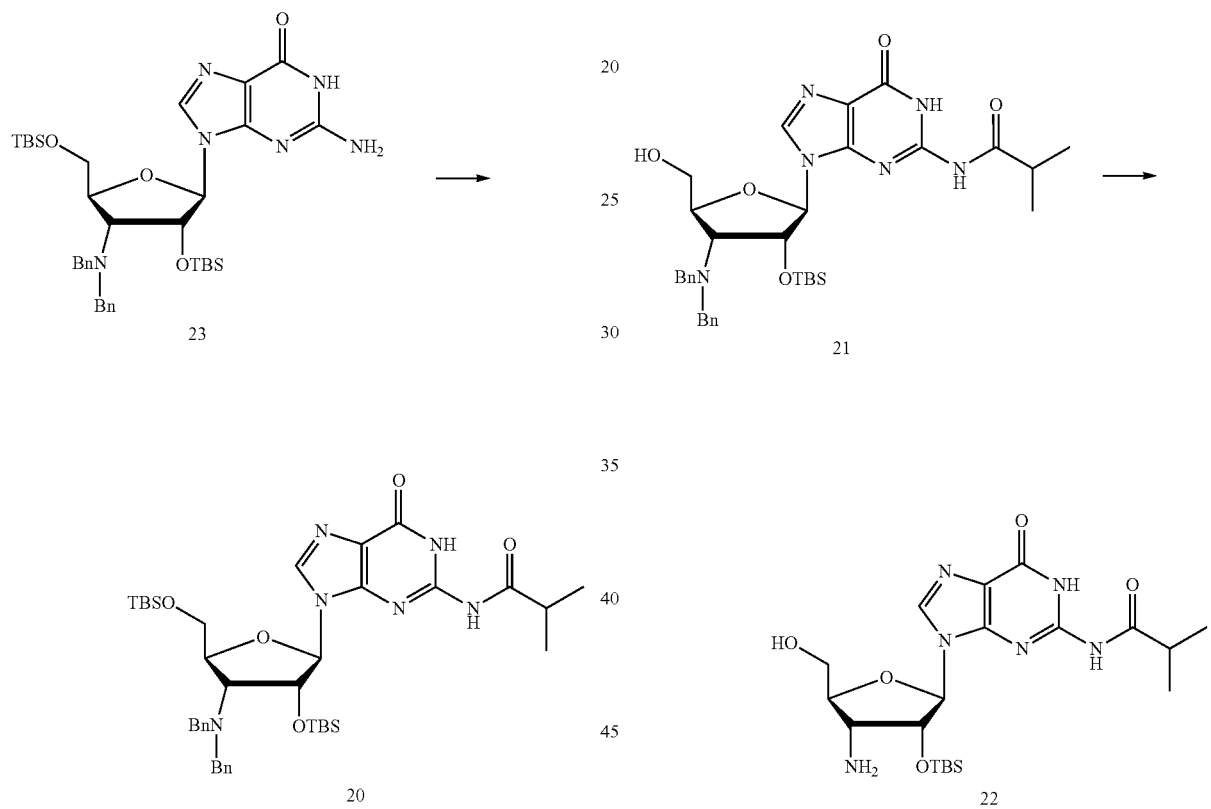

f) which is deprotected under acidic conditions to afford Compound 21 of the formula

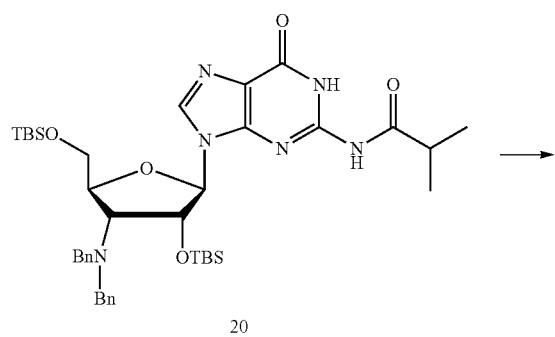

In another aspect of the invention, there are provided novel intermediate compounds and salts and diastereomers thereof as shown in the table below. While the compounds are shown with specific protecting groups, i.e., Bn for the amine substituent and TBS for the alcohol substituents, a broader range of protecting groups or none at all can be employed. For the amine protecting group (X), protecting groups can be selected from amides, thioamides, sulfonamides carbamates, imines, formamidines, alkyl (benzyl, allyl for example), phosphates and silyl compounds. For the alcohol protecting groups (Y), protecting groups can be selected from silyl, alkyl (allyl or benzyl, for example), alkoxymethyl ethers (TOM or MOM, for example), alkoxyethyl ethers (cyanoethyl, for example) and esters. These lists of protecting groups are not considered to be limiting but would also include additional ones known to those skilled in the art.

| Compound No. | Structure |
|---|---|
| 10 | 10 |
| 15 | 15 |
| 17 | 17 |
| 18 | 18 |
| 21 | 21 |

Additional aspects and embodiments of the invention are detailed below.

In one embodiment of the first aspect of the invention, there is disclosed in step a) the benzoyl protection of the primary alcohol in Compound 1, wherein the protection is accomplished through the use of benzoyl chloride and pyridine in DCM at a temperature of about 0° C. Alternatively, Bz$_2$O can be used in place of benzoyl chloride. Alternate bases include, without limiting, trimethylamine, N,N-diisopropylethylamine, 2,6 dimethylpyridine, imidazole, ethylamine. Alternate solvents include, without limiting, MeCN, THF, toluene, EtOAc and 2-MeTHF.

In another embodiment of the first aspect of the invention, there is disclosed in step b), the TEMPO mediated oxidation of the secondary alcohol in Compound 2 using TEMPO [(2,2,6,6-Tetramethylpiperidin-1-yl)oxyl] and NBS (N-bromosuccinimide) in MeCN at 23° C. Alternatively, 4-hydroxy TEMPO can be used. The oxidant PIDA ((Diacetoxyiodo)benzene) is preferred but alternate oxidants include, without limitation, NaClO, Py·SO$_3$, NCS (N-chlorosuccinimide) and PIDA. Alternate solvents include DCM, THF, toluene, EtOAc and 2-MeTHF.

In another embodiment of the first aspect of the invention, there is disclosed in step c), a reductive amination involved with imine formation using benzylamine in TFE/MeCN at about 10° C. The formed imine solution is added to a suspension of STAB-H (NaBH(OAc)$_3$) in MeCN to form the adduct. The alterative reagent for the benzylamine can be but is not limited to any benzylamine as shown below

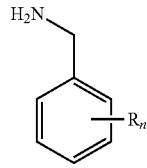

wherein R is alkyl, Cl, Br or NO$_2$ and n is 0, 1 or 2.

The alternative solvent for TFE can be but is not limited to hexafluoroisopropanol. Ti(OiPr)4 can be used as an additive to substitute the use of TFE. The additive can be a Lewis acid or a drying agent that absorbs water (such as MgSO4). The alternative reductant for STAB-H can be but is not limited toC NaBH4 and NaBH(OCOCF$_3$)$_3$. The alternative solvent for MeCN can be but is not limited to DCM, THF, toluene, EtOAc and 2-MeTHF.

In another embodiment of the first aspect of the invention, there is disclosed in step d), the benzyl protection of Compound 4 with benzyl bromide and N,N-diisopropylethylamine in MeCN at about 70° C. The alternative reagent for benzyl bromide can be benzyl chloride. An alternate for the N,N-diisopropylethylaminecan be, but is not limited to, trimethylamine, pyridine, 2,6-dimethylpyridine, imidazole or ethylamine. An alternative solvent for MeCN can be but is not limited to DCM, THF, toluene, EtOAc, 2-MeTHF. This product can be also produced by reductive animation using benzoyl aldehyde and NaBH$_4$.

In another embodiment of the first aspect of the invention, there is disclosed in step e), an acetonide deprotection of Compound 5 using TsOH hydrate in THF and toluene at rt. An alternative acid can be, but is not limited to, TFA, acetic acid or chloroacetic acid, inorganic acids and common organic acids. An alternative solvent can be any common organic solvent with water.

In another embodiment of the first aspect of the invention, there is disclosed in step f), a benzoyl protection reaction using benzoic anhydride, $Et_3N$, and DMAP in toluene at rt. Alternative reagents for benzoic anhydride can be BzCl and BzOH. Alternate bases that can be used include, but are not limited to, N,N-diisopropylethylamine, 2,6 dimethylpyridine, imidazole and ethylamine. Alternate solvents that can be used include, but are not limited to, MeCN, THF, toluene, EtOAc and 2-MeTHF.

In one embodiment of the second aspect of the invention, there is disclosed in step a), Vorbrüggen chemistry using $HA^{Bz}$, BSA and TMSOTf in MeCN at 70° C. An alternative reagent for TMSOTf can be, but is not limited to, TBSOTf and $SnCl_4$. Alternate solvents that can be used include, but are not limited to, xylenes, toluene and THF. An alternative additive can be, but is not limited to, DBU.

In another embodiment of the second aspect of the invention, there is disclosed in step b), a benzoyl deprotection using KOH and MeOH at about 60° C. An alternative for KOH can be, but is not limited to, common inorganic bases, like NaOH, LiOH, $K_2CO_3$, $Ba(OH)_2$ and the like. Alternate solvents can be, but are not limited to, EtOH and IPA.

In another embodiment of the second aspect of the invention, there is disclosed in step c), a TBS protection of Compound 10 using TBSCl and imidazole in $PhCF_3$ and NMP. One alternative condition is to use TBSOTf and 2,6-lutidine in DCM.

In another embodiment of the second aspect of the invention, there is disclosed in step d), a protection step using BzCl and lutidine in toluene. The alternative reagent for BzCl can be $Bz_2O$. and any common organic base can be used. Alternate solvents can be, but are not limited to, THF, 2-MeTHF, DCM and xylene.

In another embodiment of the second aspect of the invention, there is disclosed in step f), a hydrogenation step using $PdCl_2$ and $ZnBr_2$ in DMF under hydrogen pressure. The $PdCl_2$ can be exchanged to any possible Pd/C. Alternatives to $ZnBr_2$ include, but are not limited to, TsOH, LiCl, LiBr, imidazole hydrochloride, $ZnI_2$ or $ZnCl_2$, other transition metal salts or rare earth metal salts. Alternate solvents can be, but are not limited to, THF, toluene, DCM, TFE, AcOH and IPAc.

In one embodiment of the third aspect of the invention, there is disclosed in step a), Vorbrüggen chemistry using $HA^{Bz}$, BSA and TMSOTf in MeCN at 70° C. An alternative reagent for TMSOTf can be, but is not limited to, TBSOTf and $SnCl_4$. Alternate solvents that can be used include, but are not limited to, xylenes, toluene and THF. An alternative additive can be, but is not limited to, DBU.

In another embodiment of the third aspect of the invention, there is disclosed in step b), a hydrolysis reaction using water and TFA in toluene. Alternate acids include any common inorganic acid and alternate solvents that can be used include, but are not limited to MeOH, EtOH, THF, 2-MeTHF and MeCN.

In another embodiment of the third aspect of the invention, there is disclosed in step c), a deprotection step using aqueous KOH in toluene. Alternate bases that can be used include, but are not limited to common soluble inorganic bases such as aq. LiOH, aq. NaOH, $K_2CO_3$ and other carbonate bases.

In another embodiment of the third aspect of the invention, there is disclosed in step d), a TBS protection of Compound 18 using TBSCl and imidazole in $PhCF_3$ and NMP at about 100° C. Alternatively, the protection step can use TBSOTf and 2,6-lutidine in DCM.

In another embodiment of the third aspect of the invention, there is disclosed in step e), another protection step using iBuCOCl and pyridine. Alternatively, this step can use $(iBuCO)_2O$ and trimethylamine or N,N-diisopropylethylamine as the base.

In another embodiment of the third aspect of the invention, there is disclosed in step f), the deprotection of TBS in Compound 20 utilizing TFA in water and DCM at about 23° C. Alternatively, common organic acids and common organic solvents can be utilized. Finally, in another embodiment of the third aspect of the invention, there is disclosed in step g), a hydrogenation reaction using Pd/C and $TsOH \cdot H_2O$ in THF under hydrogen pressure. Alternatively, any Pd/C can be used. Alternate solvents that can be used include, but are not limited to MeOH, EtOH, IPA, toluene, DCM and IPAc.

DETAILED DESCRIPTION OF THE INVENTION

Examples

The invention will now be further described by the following working example(s), which are preferred embodiments of the invention. All temperatures are in degrees Celsius (° C.) unless otherwise indicated. These examples are illustrative rather than limiting and it is to be understood that there may be other embodiments that fall within the spirit and scope of the invention as defined by the claims appended hereto.

For ease of reference, the following abbreviations may be used herein.

| Abbreviations | Name |
|---|---|
| $CH_3CN$, MeCN/ACN | Acetonitrile |
| aq. | Aqueous |
| Bn | Benzyl |
| BSA | N,O-Bis(trimethylsilyl)acetamide |
| Bu | Butyl |
| Bz | Benzoyl |
| BzCl | Benzoyl chloride |
| Cbz | benzyl carbamate |
| conc. | Concentrated |
| DBU | 1,8-Diazabicyclo[5.4.0]undec-7-ene |
| DCE | Dichloroethane |
| DCM | Dichloromethane |
| DIPEA | N,N-Diisopropylethylamine |
| DMAP | 4-N,N-dimethylaminopyridine |
| DMF | dimethyl formamide |
| DMSO | dimethyl sulfoxide |
| eq. | Equivalents |
| Et | Ethyl |
| EtOAc | ethyl acetate |
| EtOH | Ethanol |
| $Et_2O$ | diethyl ether |
| $Et_3N$ | Triethylamine |
| h | hour(s) |
| $HA^{Bz}$ | 6-Benzylaminopurine |
| $HG^{Cl}$ | 2-Amino-6-chloropurine |
| HPLC | high pressure liquid chromatography |
| $H_2SO_4$ | sulfuric acid |
| IPAc | isopropyl acetate |
| i-PrOH | Isopropanol |
| KF, Kf, kf | Karl Fischer |
| Me | Methyl |
| MeOH | Methanol |
| MTBE | methyl t-butyl ether |
| NMI | 1-Methylimidazole |
| NMP | N-Methyl-2-pyrrolidone |
| NMR | nuclear magnetic resonance |
| $Pd/Al_2O_3$ | palladium on alumina |

-continued

| Abbreviations | Name |
|---|---|
| Pd/C | palladium on carbon |
| PdCl$_2$ | Palladium(II) chloride |
| Ph | Phenyl |
| PhCF3 | Trifluorotoluene |
| RAP | Relative area percent |
| rt/RT | room temperature |
| sat. | Saturated |
| STAB | sodium triacetoxyborohydride |
| t-Bu | tertiary butyl |
| t-BuOH | tertiary butanol |
| TBS | Tert-butyldimethylsilyl |
| TBSCl | tert-Butyldimethylchlorosilane |
| TBSOTf | tert-Butyldimethylsilyl trifluoromethanesulfonate |
| TMSOTf | Trimethylsilyl trifluoromethanesulfonate |
| TFA | trifluoroacetic acid |
| THF | Tetrahydrofuran |
| TEMPO | 2,2,6,6-Tetramethyl-1-piperidinyloxy |
| TFE | Trifluoroethanol |
| Ti(OiPr)4 | Titanium(IV) isopropoxide |
| TsOH | p-toluenesulfonic acid |

Experimental Section

General: All reactions were performed under a nitrogen atmosphere using anhydrous techniques unless otherwise noted. Reagents were used as received from the vendors, unless otherwise noted. Quoted yields are for isolated material, and have not been corrected for moisture content. Reactions were monitored by GC or reverse phase HPLC on a Shimadzu system using CH$_3$CN/H$_2$O/MeOH as the mobile phase (containing either 0.05% TFA, or 0.1% NH$_4$OAc). NMR-spectra were recorded on Bruker DRX-600 or DRX-500 instruments, and are referenced to residual undeuterated solvents. The following abbreviates are used to explain multiplicities: br=broad, s=singlet, d=doublet, t=triplet, q=quartet, m=multiplet. High resolution mass spectra (HRMS) were recorded on a Thermo Orbi-trap Discovery instrument. Melting points were recorded using a Thomas Hoover melting point apparatus and are uncorrected. The quantitative analysis of residual palladium catalyst was performed with a Perkin-Elmer Optima 4300 DV ICP-AES instrument.

Overall Scheme

Overall Synthetic Scheme
Synthesis of key intermediate 8

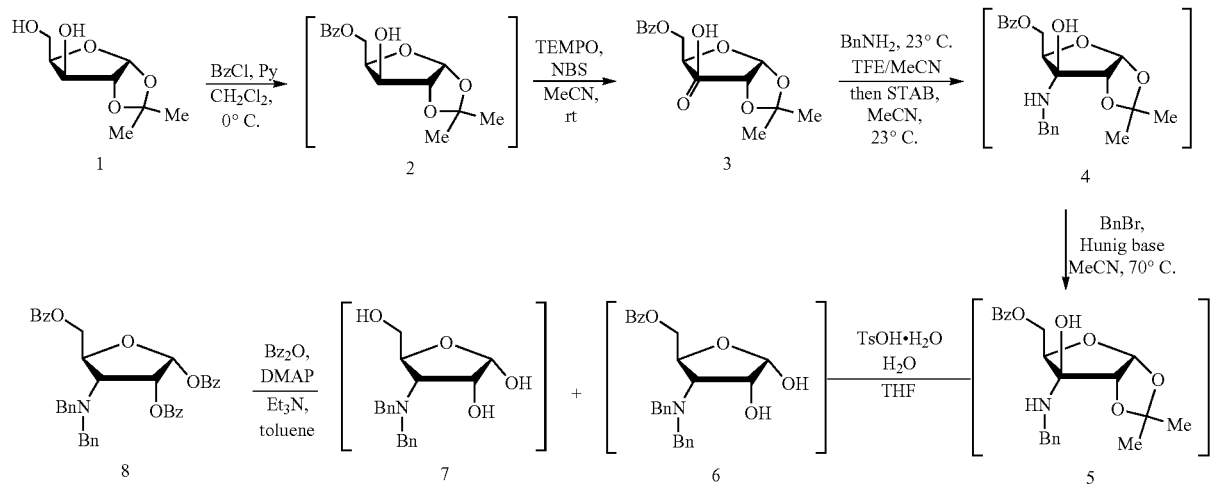

Synthesis of adenosine aza nucleoside 15

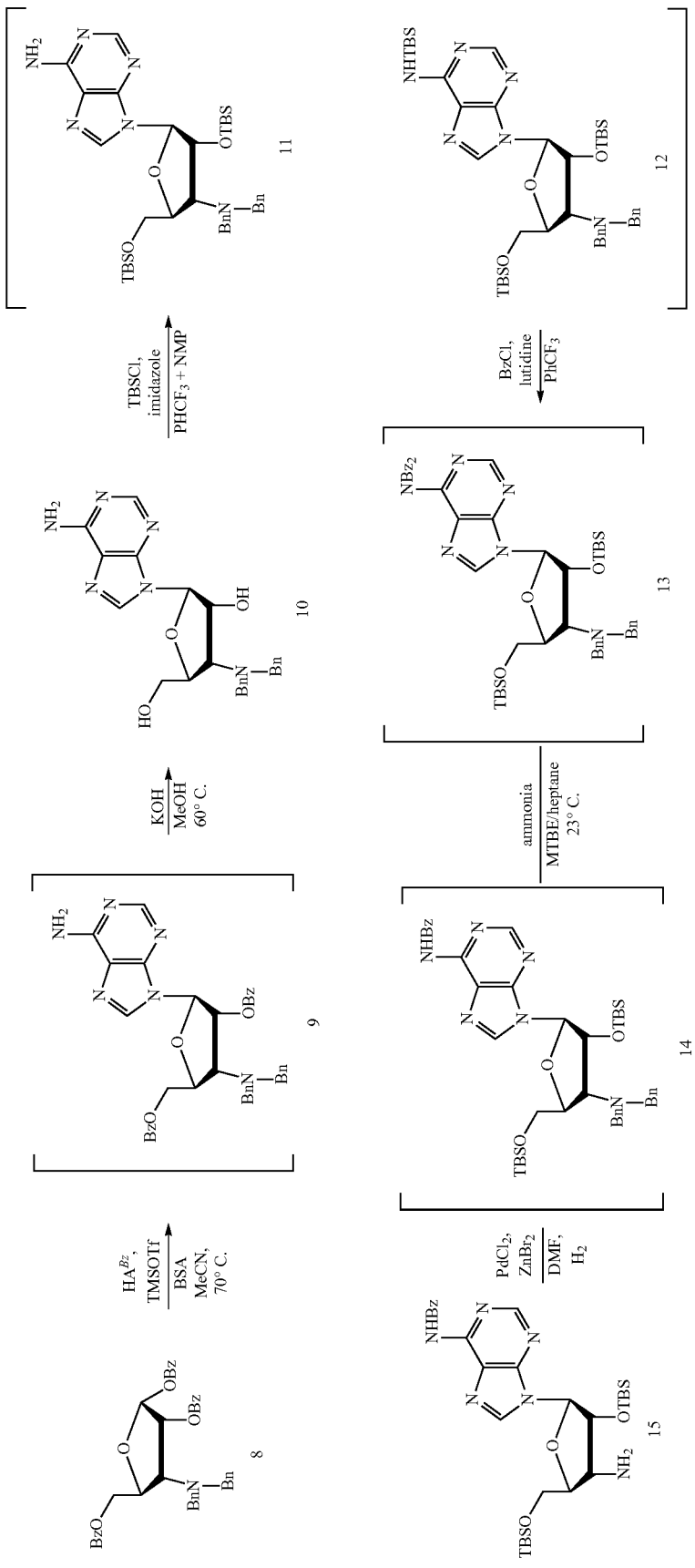

Synthesis of guanosine aza nucleoside 22

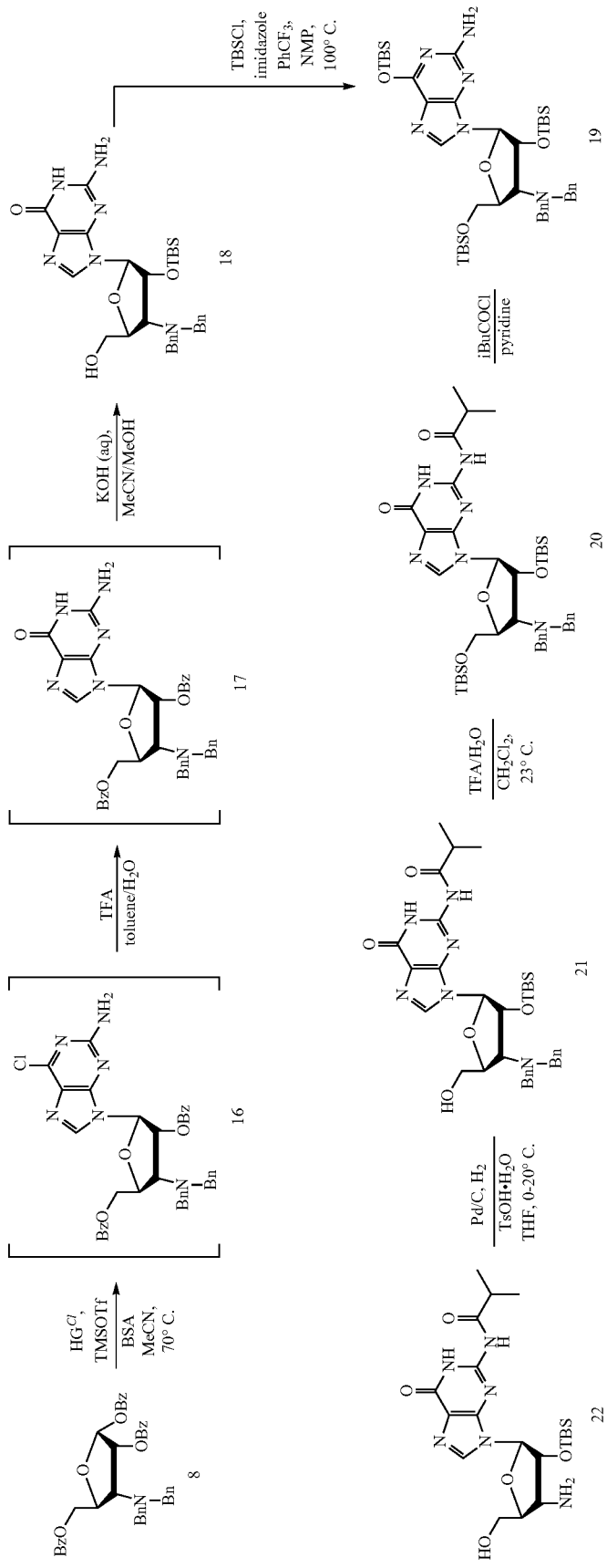

Example 1

Synthesis of Compound 2:

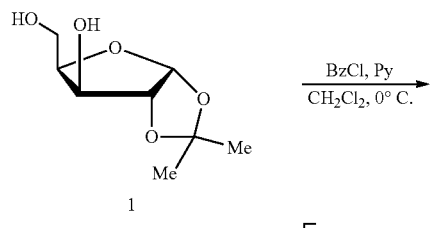

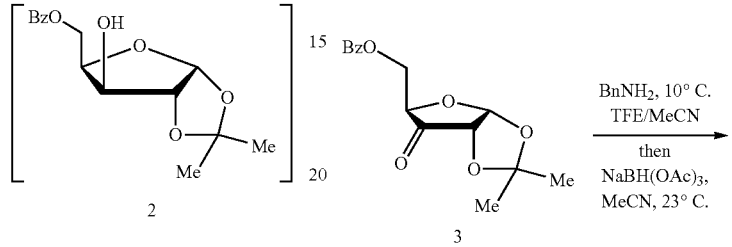

To a N$_2$ flushed 50 L reactor, CH$_2$Cl$_2$ (5.0 L) was added. Xylofuranose 1 (1.0 kg, LR) and pyridine (0.83 kg, 2.0 eq.) were charged into the reactor. Benzoyl chloride (0.78 kg, 1.05 eq.) was slowly added to the reactor at −10° C. in 1 h and quenched the reaction until the TLC indicated the reaction to finish. To the cold solution, water (1 kg) was added. Layers partitioned and the organic stream was washed with citric acid (3.0 L, 10% wt, aq.), NaHCO3 (3.0 L, 10% wt, aq.), and brine (2.0 L, 15% wt, aq.). The crude will be used in the next step without further purifications.

Example 2

Synthesis of Compound 3

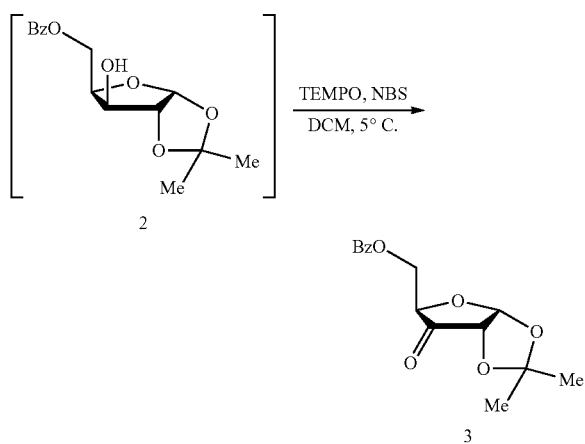

The solution of 2 (1.0 kg, LR) in CH$_2$Cl$_2$ (4.0 L) was charged to the reactor. To the reactor was added CH$_2$Cl$_2$ (2.0 L) and water (2.0 L). To the mixture, was subsequently added NaHCO$_3$ (0.44 kg, 1.0 eq.) and TEMPO (0.041 kg, 0.05 eq.) and the mixture was cooled to −5° C. To the mixture, NBS (0.94 kg, 1.0 eq.) was added slowly in 1 hour maintaining the temperature between −5 to 5° C. After 2 hours, the solution was washed with Na$_2$SO$_3$ (1.0 L) and layers were separated. The aqueous solution was back extracted with CH$_2$Cl$_2$ (2.0 L) and the organic layers were combined. The organic phase was washed with brine (2.0 L) and solvent swapped to MTBE (6.0 L). Slow addition of heptane (4.0 L) at 45° C. gave a suspension which was slowly cooled to 15° C. The solid was filtered and washed with MTBE/heptane (3.0 L). The solid was dried in oven for 20 hours to give off-white solid (0.60 kg, 61%).

Example 3

Synthesis of Compound 4

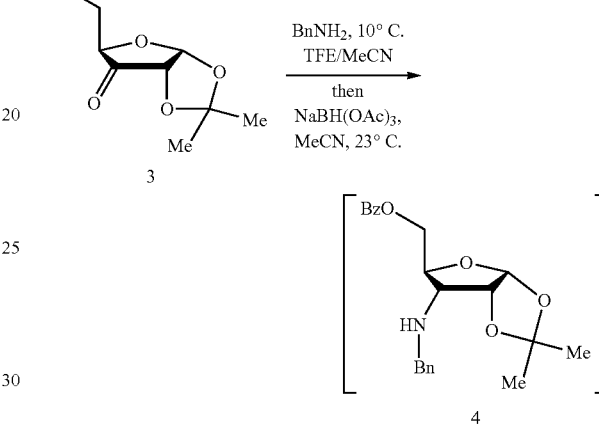

In the N$_2$ flushed reactor, MeCN (3.0 L), 3 (1.0 kg, LR), TFE (1.0 L), BnNH$_2$ (0.44 kg, 1.2 eq) were charged in such sequence at 10° C. After 6 h, HPLC confirmed no more than 7% of Compound 3 was in the solution. The solution was immediately cooled to 0° C. In a separate reactor, MeCN (5.0 L) and STAB (2.17 kg, 3.0 eq.) were added. To the suspension at 23° C., the imine solution was transferred in about 1 h. After transfer, the reaction was agitated for an extra 1 h. Then the solution was washed with citric acid (5.0 L, 5 wt %, aq.) and brine (3.0 L). The resulting organic solution was washed with Na$_2$CO$_3$ (3.0 L, 15 wt %, aq.) and separated while controlling the pH between 7-8. The organic stream was washed with NaHCO$_3$ (3.0 L, 6% wt, aq.) and 20 wt % brine (3.0 L) The batch was distilled to a MeCN solution (2.0 L) and used in the next step without further purification.

An Alternative Condition for the Synthesis of Compound 4:

To a N$_2$ flushed reactor was charged THF (5.0 L) and Compound 3 (1.0 kg, LR). Ti(OiPr)$_4$ (0.78 kg, 0.8 equiv) was charged and the mixture was cooled to 0° C. BnNH$_2$ (0.44 kg, 1.2 equiv) was charged and the mixture was agitated for 2 h, or until HPLC confirmed no more than 2% compound 3 was left in the mixture. To another N$_2$ flushed reactor was charged THF (5.0 L) and STAB (3.63 kg, 5.0 equiv). To the suspension was added the imine solution in about 1 h. After transfer, the reaction was agitated for an extra 1 h. Then the solution was washed with citric acid (5.0 L, 5 wt %, aq.) and brine (3.0 L). The resulting organic solution was washed with Na$_2$CO$_3$ (3.0 L, 15 wt %, aq.) and separated while controlling the pH between 7-8. The organic stream was washed with NaHCO$_3$ (3.0 L, 6% wt, aq.) and 20 wt % brine (3.0 L). The solvent of the crude was distilled to a MeCN (2.0 L) solution and will be used in the next step without further purifications.

Example 4

Synthesis of Compound 5

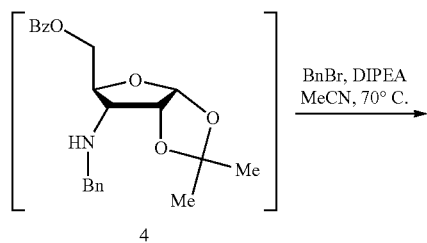

To the solution from Example 3, MeCN (0.5 L), DIPEA (1.0 kg, 3.0 eq.) and BnBr (0.89 kg, 2.0 eq.) were added to the reactor. The reactor was warmed to 70° C. for 7 h. The solution was cooled to 20° C. and charged Et$_3$N (0.26 kg, 1.0 eq.) in 30 min. After 12 h, the solution was added toluene (5.0 L) and stirred for 30 min. The solution was washed with citric acid (2.0 L/kg, 20 wt %, aq.) and 20 wt % brine (2.0 L). The resulting organic solution was concentrated and swapped to toluene (2.0 L). The solution was used in the next step without further purifications.

Example 5

Synthesis of Compound 6

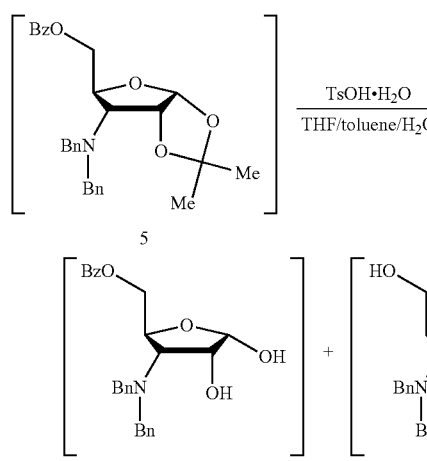

To the crude solution from Example 4, THF (1.0 L) and water (0.5 L) were charged into the reactor. TsOH·H$_2$O (0.80 kg, 3.0 eq.) was added to the reactor and the solution was aged at 60° C. for 8 h. The solution was then cooled to 10° C., and neutralized with 5% NaHCO$_3$ (aq.) until pH 7-8 and the organic layer was separated. The organic layer was washed with 20 wt % brine (2.0 L) and the solution was used in the next step without further purifications.

Example 6

Synthesis of Compound 8

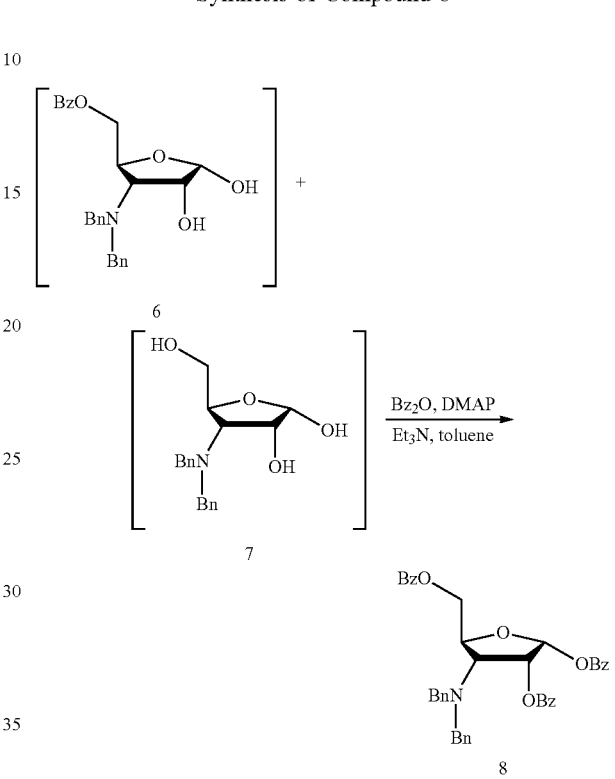

To the solution was added DMAP (0.014 kg, 0.05 eq.), Et$_3$N (0.070 kg, 3.0 eq.) and Bz$_2$O (1.14 kg, 2.0 eq.). The crude was aged at 25° C. for 6 h. To the crude was charged THF (5.0 L). The solution was washed with 20 wt % brine (5.0 L) and separated. The organic solution was washed with citric acid+NaCl mixed solution (citric acid 5 wt %, NaCl solution 15% wt %, aq) and separated. The crude was washed again with 20 wt % brine and separated. The solvent of the crude was swapped to 2-MeTHF (1.5 L). At 70° C., heptane (3.0 L) was added dropwise in 30 min. The solution was cooled to 25° C. in 2 h. The slurry was filtered and the solid was dried in the oven. After 4 steps, a brown solid 8 (2.58 kg, 48%) was isolated.

Example 7

Synthesis of Compound 9

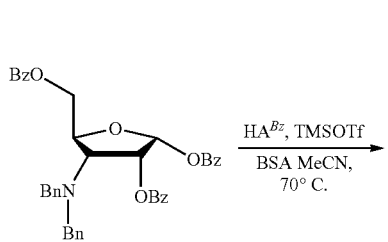

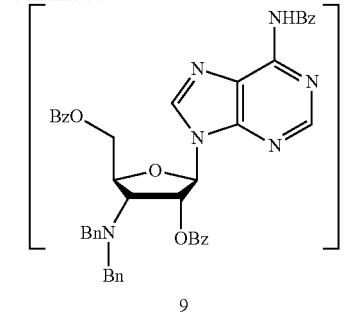

In the reactor, MeCN (8.0 kg) and compound 8 (1.0 kg, LR) were charged to give a solution. To the solution were added, HA$^{Bz}$ (0.37 kg, 2 eq.) and BSA (0.54 kg, 1.5 eq.). The suspension was heated to 65° C. for 2 h. and TMSOTf (0.36 kg, 1.0 eq.) was added. The solution was heated to 70° C. for 6 h. The solution was cooled to 25° C. and quenched with NaHCO$_3$ (5.0 L, 5% wt, aq.). To the mixture, i-PrOAc (8.0 L) was charged and the organic solution was separated. The aqueous layer was extracted with i-PrOAc (2.0 L) and the combined organic layers were washed with NaHCO$_3$ (5.0 L, 5% wt, aq.) and brine. The organic solution was concentrated to 2.0 L and solvent swapped to MeCN.

The solution was used in the next step without further purifications.

Example 8

Synthesis of Intermediate 10

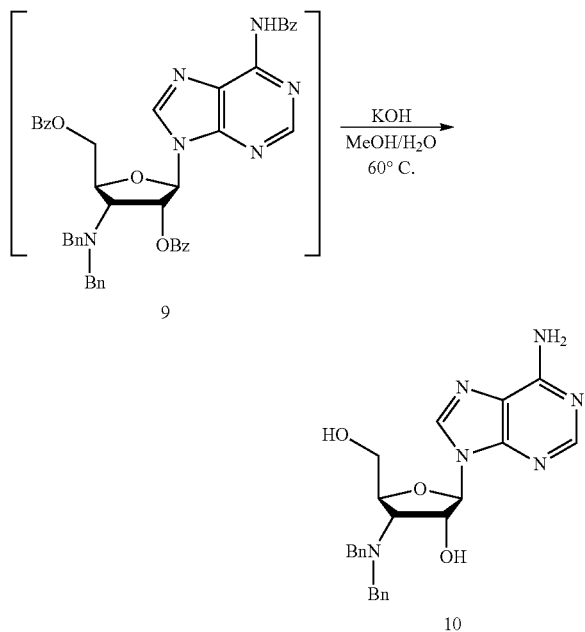

To the solution of 9 from Example 7, MeOH (4.0 L) and water (0.5 L) were added to give a homogenous solution. KOH solution (0.35 kg solid, dissolved in 0.15 L water, 4.0 eq.) was slowly added to the solution at 25° C. in 10 min. The solution was aged at 60° C. for 5 h. Next, the solution was cooled to 0° C., and water (15.0 L) was introduced slowly to maintain the internal temperature. Then the suspension was further agitated for 1 h. The solid was filtered and washed with water (1.0 L). The solid was dried to KF<5 wt %, then suspended in MTBE (6.0 L) and warmed to 45° C. for 1 h. The slurry was cooled to 23° C. and filtered. The solid was washed with MTBE (1.0 L) and dried in the oven to afford a pale brown solid (464 g, 64% for two steps).

Example 9

Synthesis of Compounds 11 and 12

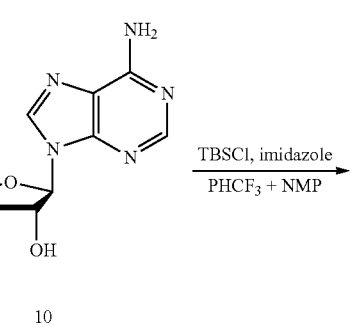

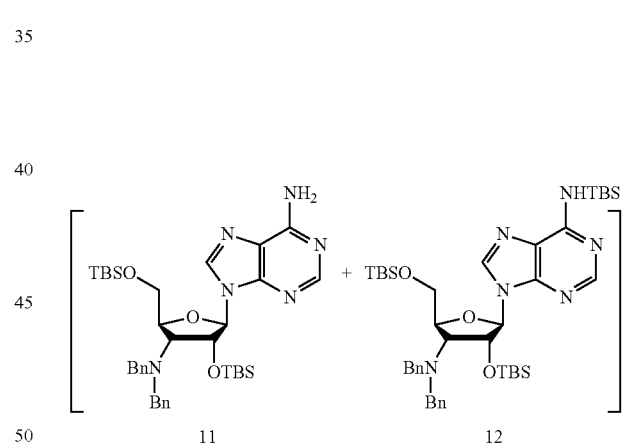

In the reactor, compound 10 (1.0 kg, LR) was dissolved in PhCF$_3$ (5.0 L). Imidazole (1.5 kg, 10.0 eq.) and TBSCl (1.7 kg, 5.0 eq.) were charged to the reactor. The suspension was diluted with NMP (1.0 L). The solution was aged at 100° C. for 18 h and cooled down to 23° C. The crude was added MeOH (2.5 L) and aged for 1 h. To the reaction mixture, water (1.0 L) and heptane (5.0 L) were charged into the reactor. Layers were partitioned and separated. To the aqueous layer was added heptane (2.5 L), and the layers were partitioned and separated. To the combined organic layers were added celite (1.0 kg) and 20 wt % brine (5.0 L). The biphasic mixture was filtered and layers were separated. The organic layer was solvent swapped to PhCF$_3$ and concentrated to 2.0 L. The material will be used in the next step without further purifications.

Example 10

Synthesis of Compound 13

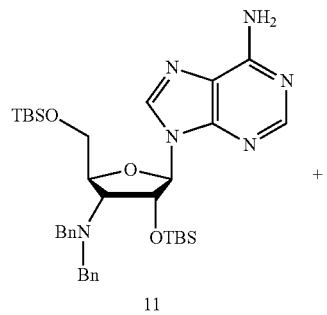

11

+

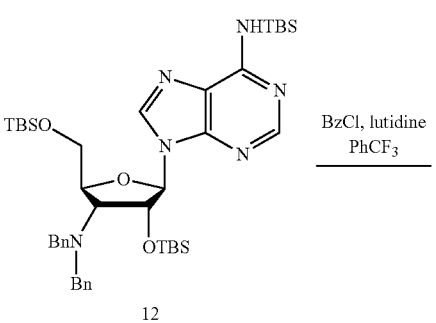

12

→ (BzCl, lutidine, PhCF₃)

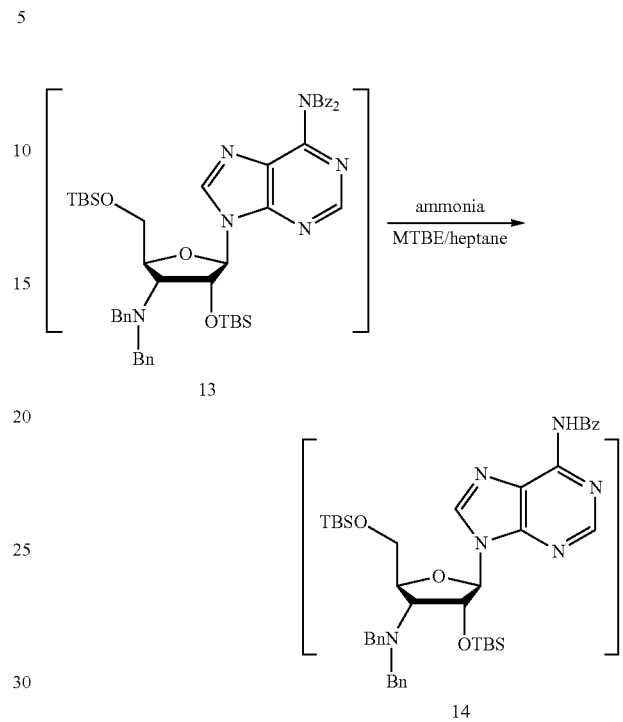

13

In the reactor, the crude stream containing 11 and 12 from Example 9 was charged. An additional amount of PhCF₃ (8.0 L) was added to give a diluted solution. To the solution, 2,6-lutidine (0.96 kg, 4.0 eq.) and BzCl (0.96 kg, 3.0 eq.) were added. The solution was agitated at 100° C. for 4 h. The solution was cooled to 35° C. and charged with MTBE (10.0 L). The organic solution was washed with 5 wt % aqueous NaHCO₃ (10.0 L) and 20 wt % brine. The resulting organic mixture was concentrated to 2.0 L and swapped to heptane. The solution was used in the next step without further purifications.

Example 11

Synthesis of Compound 14

To the crude stream of 13 from Example 10, heptane (6.0 L) and MTBE (4.0 L) were added to the reactor. To the solution was added ammonia in MeOH (0.0132 L, 6.0 eq.) dropwise at 0° C. The solution was agitated at 0° C. for another 7 h. Then the reaction mixture was suspended with celite (1.0 kg) and 5 wt % aqueous citric acid (5.0 L). The biphasic suspension was filtered and layer were separated. The organic solution was washed with 20 wt % brine (5.0 L) and concentrated to 2.0 L and swapped to heptane. The solution was used in the next step without further purifications.

Example 12

Synthesis of Compound 15

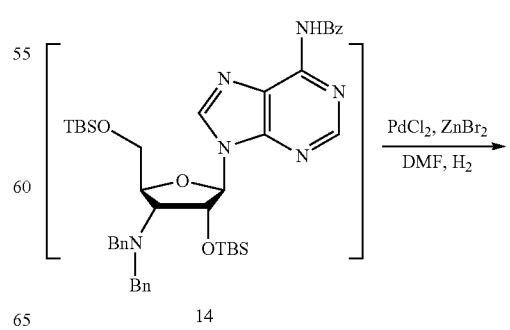

14

→ PdCl₂, ZnBr₂, DMF, H₂

-continued

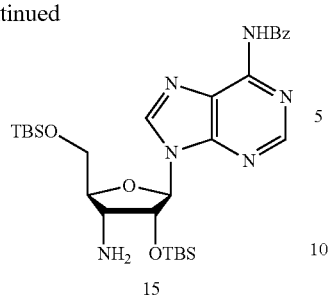

15

The solution of 14 (1.0 kg, LR) from Example 11 was swapped to DMF (8.0 L) and transferred to a hydrogenation reactor. $PdCl_2$ (0.023 kg, 0.1 eq.) and $ZnBr_2$ (0.072 kg, 0.25 eq.) were added to the solution, to afford a suspension. The suspension was cooled to 0° C. and the reactor was rinsed with DMF (2.0 L) and backfilled with $H_2$ three times. The reaction was aged for 6 h. The crude was backfilled with $N_2$ three times. MTBE (10.0 L) was added to the solution and the organic solution was washed with $Na_2S_2O_3$ (5.0 L, 10 wt %, aq.) and 20 wt % brine (5.0 L). The organic stream was concentrated and purified by silica gel chromatography with $CH_2C_2$/MeOH (100/0 to 5/95) to give 15 as pale yellow solid (0.71 kg, 78%).

An alternative Bn deprotection condition is included in the scale-up section.

Example 13

Synthesis of Compound 16

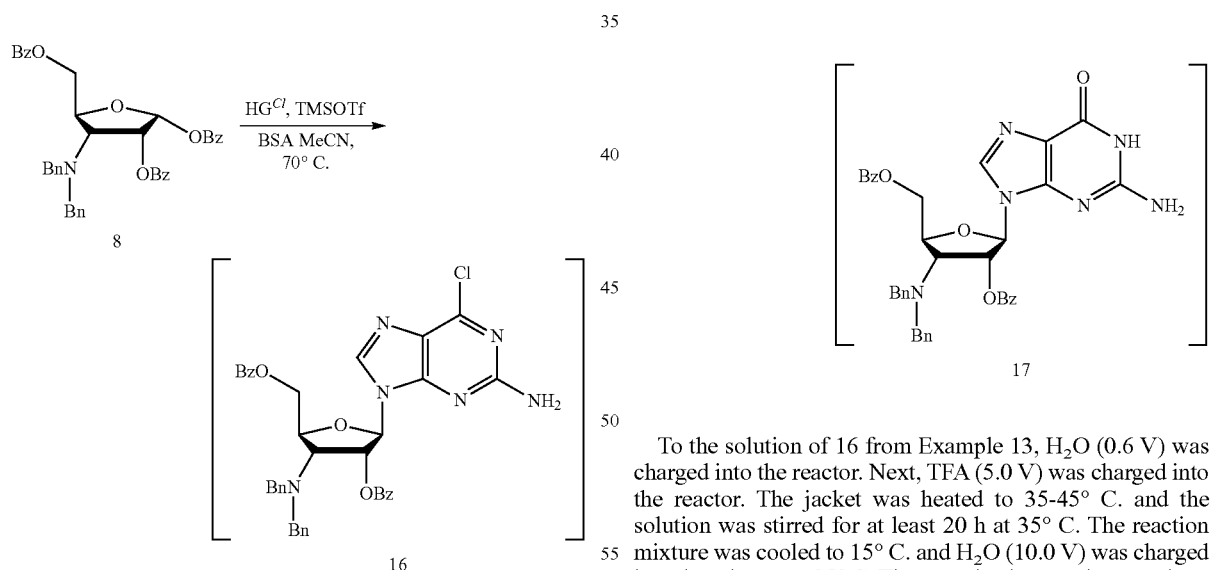

MeCN (8.0 kg) and compound 8 (1.0 kg, LR) were charged to the reactor to give a solution. To the solution were added, $HG^{Cl}$ (0.26 kg, 2.0 eq.) and BSA (0.54 kg, 1.5 eq.). The suspension was heated to 65° C. for 2 h. Then, TMSOTf (0.36 kg, 1.0 eq.) was added and the solution was heated to 70° C. for 7 h. The solution was cooled to 25° C. and quenched with $NaHCO_3$ (5.0 L, 5% wt, aq.). To the mixture, toluene (8.0 L) was charged and the layers were separated. The aqueous layer was back-extracted with toluene (2.0 L) and the combined organic layers were washed with $NaHCO_3$ (5.0 L, 5% wt, aq.) and 20 wt % brine. The solution was concentrated to 2.0 L and solvent swapped to toluene. The solution was used in the next step without further purifications.

Example 14

Synthesis of Compound 17

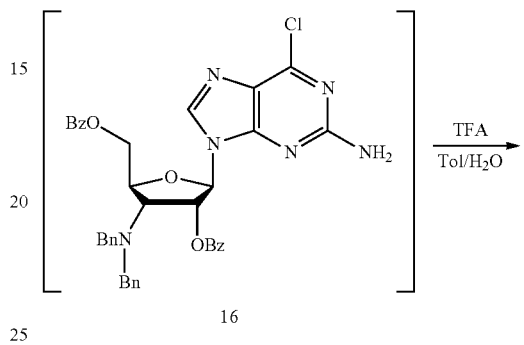

To the solution of 16 from Example 13, $H_2O$ (0.6 V) was charged into the reactor. Next, TFA (5.0 V) was charged into the reactor. The jacket was heated to 35-45° C. and the solution was stirred for at least 20 h at 35° C. The reaction mixture was cooled to 15° C. and $H_2O$ (10.0 V) was charged into the mixture at 25° C. The organic phase and water phase were separated. To the aqueous phase, toluene (4.0 V) was charged and the solution was stirred for at least 30 minutes at 15° C. The organic phase was separated and all organic phase were combined and washed with water (10.0 V). The organic phase was then washed with 5% (w/w) aqueous $K_3PO_4$ and 15% (w/w) brine (aq. 4 V). The organic solution was concentrated to 2.0 V under vacuum at NMT 60° C. The concentrated solution was slowly added to heptane (10.0 V) to afford crystallization in 2 h at 25° C. The solid was filtered and washed with heptane (2.0 V) to give a light brown solid (890 g, 79%).

Example 15

Synthesis of Compound 18

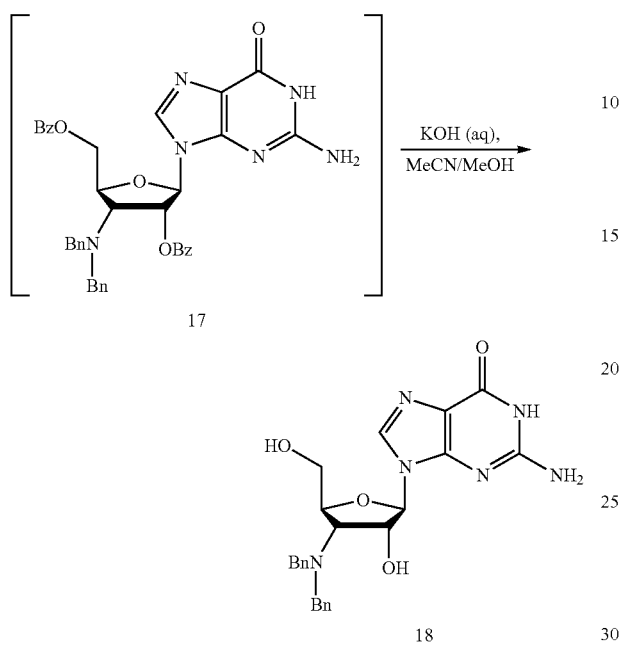

To the reaction was charged MeCN (2.0 L/kg, 2 vol) and MeOH (3.0 L/kg, 3 vol). The solution was agitated and Compound 17 (0.891 kg, LR) was charged into the reactor. Next, the KOH solution (0.65 L/kg, 0.65 vol, 2.6 eq KOH) was charged into the reactor at 25-35° C. The solution was heated to 55-65° C. for 2 h. The reaction mixture was cooled to 15-25° C. and 1 M aq. HCl (1.0-2.0 L/kg, 1.0-2.0 vol) was added dropwise to the reactor to adjust the pH to 7-8 while maintaining the internal temperature between 15-25° C. The solid precipitated during pH adjustment and was filtered and washed with MeCN/MeOH (v/v=1/1, 2.0 L/kg, 2.0 vol). The crude solid was added into the reactor and 5% (w/w) $Na_2CO_3$ (10.0 L/kg, 10.0 vol) was charged into the reactor. The resulting suspension was heated to 65-75° C. for 3 h and the reaction mixture was cooled to 15-25° C., and then agitated for no less than 1 h. The solid was filtered and the cake was washed with water (2.0 L/kg, 2.0 vol) and dried in an oven to give a light brown solid. The solid was then dissolved with NMP (4.0 L/kg, 4.0 vol) at 60-70° C. for no less than 20 min. The solution was cooled to 40-50° C. and the pH adjusted to 7-8 with AcOH. The solution was cooled to 15-25° C. and agitated for no less than 1 h. MTBE (15 L/kg, 15.0 vol) was added dropwise to the reactor and the suspension was agitated for no less than 2 h at 15-25° C. The solid was filtered and the cake was washed with MTBE (2.0 L/kg, 2.0 vol). The solid was dried in an oven under vacuum to give a light brown solid (0.86 kg, 87%).

An Alternative Conditions for the Synthesis of Compound 18:

To the reaction was charged MeCN (2.0 L) and MeOH (3.0 L). The solution was agitated and Compound 17 (1.0 kg, LR) was charged into the reactor. Next, the $K_2CO_3$ (1.65 kg, 8 equiv) and water (8.0 L) were charged into the reactor at 25-35° C., and the mixture was heated to 70-80° C. for 5 h. The homogeneous reaction mixture was cooled to 60° C. and seeded with 1 wt % Compound 18 (0.01 kg). After 1 h, the mixture was cooled slowly to 40-50° C. for 1 h and held at the temperature for 1 h. Then the mixture was cooled slowly to 15-25° C. for 3 h. Water (10.0 L) was charged in 1 h and the slurry was agitated for 2 h before filtration. The resulting wet cake was washed with water (5.0 L×2) and dried in an oven under vacuum to give a yellow solid (0.59 kg, 85%).

Example 16

Synthesis of Compound 19

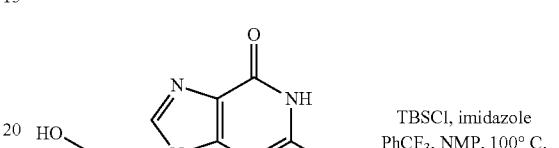

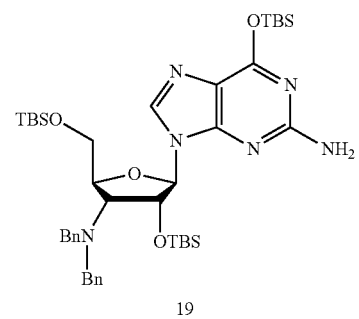

NMP (3.0 L/kg, 3.0 vol) was charged to the reactor and the solution was heated to 55-65° C. Agitation was started and Compound 18 (1.0 kg, LR) and imidazole (1.46 kg, 10.0 equiv) were charged into the reactor. Next, $CF_3Ph$ (1.0 L/kg, 1.0 vol) and TBSCl (1.63 kg/kg, 5.0 eq.) were charged to the reactor. The solution was stirred for no less than 5 h at 100° C. The reaction mixture was cooled to 15-25° C. MTBE (10.0 L/kg, 10.0 vol) and MeOH (1.0 L/kg, 1.0 vol) were charged into the reactor and agitated for 15 min. Then 10% (w/w) aqueous citric acid (8.0 L/kg, 8.0 vol) was charged into the reactor for no less than 30 min. The layers were partitioned and the organic layer was retained. The organic layer was washed with water (5.0 kg/L, 5.0 vol) and was concentrated under vacuum to 2 L/kg. To the crude was added THF (5 L/kg, vol) and the batch was concentrated under vacuum to 2.0 L/kg. The solution was used in the next step without further purifications.

Example 17

Synthesis of Compound 21

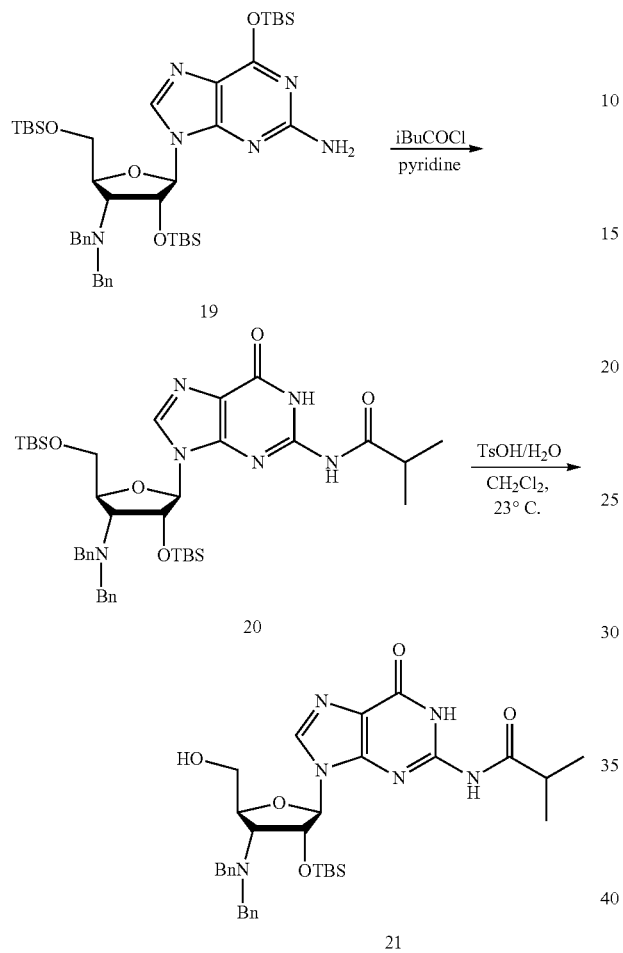

Under N2, the THF solution (2 L/kg) containing Compound 19 from Example 16 and pyridine (3 L/kg) were charged and the mixture was cooled to 0-10° C. Isobutyryl chloride (0.69 kg, 3.0 equiv) was charged dropwise into the mixture under 0-10° C. The solution was warmed to 10-20° C. and THF (3.0 L) was charged to the reaction. The reaction mixture was cooled to 0-10° C. 1 L/kg NH3·H2O (10%) was charged dropwise to the reaction mixture at 0-10° C. and the reaction was agitated until no bis-protected intermediate was observed. MTBE (5.0 L, 5V) and water (10.0 L, 10 V) were charged to the mixture. Layers partitioned and the aqueous phase was extracted with MTBE (5.0 L, 5V). The organic phases were combined and washed with 30 wt % critic acid aqueous solution two times (10.0 L×2). The organic phase was then washed with water (10 L, 10 V) and concentrated to 2.0 L.

DCM (8.0 L, 8 V) and water (1.0 L, 1 V) were added to the previous mixture. The solution was cooled to 0-10° C., and TsOH (4.0 eq.) was charged to the mixture and agitated for 3 h. DIPEA was added dropwise to the mixture at 0-10° C., to adjust the pH of the mixture to 7-8. Water (10 L, 10 V) was added and the organic phase was separated. The organic phase was concentrated to 2V and iPrOH (5.0 L, 5V) was charged to the mixture. The mixture was concentrated to 3V and the slurry was filtered. The solid was dried in an oven under vacuum to give a light brown solid (0.71 kg, 76%).

Example 18

Synthesis of Compound 22

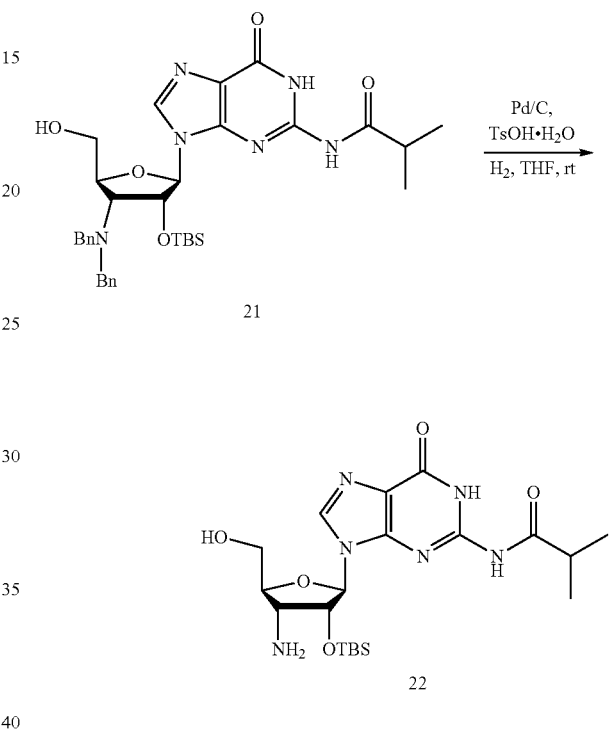

Compound 21 (1.0 kg, LR) was dissolved in THF (10.0 L) and transferred to a hydrogenation reactor. Pd on carbon (0.10 kg, 0.1 equiv) and TsOH·H2O (0.28 kg, 1.0 equiv) were added to the solution, to afford a suspension at 23° C. and the reactor was backfilled with H2 three times. The reaction was agitated for 6 h. The reaction mixture was backfilled with N2 three times. The mixture was filtered (through diatomite 1.0 w/w) and the cake washed with THF (2*2.0 L). TMT-Na and NaCl aqueous solution (aq, 5.0 L, 1% TMTNa, 10 wt % NaCl, w/w) were charged to the mixture, and the biphasic mixture was stirred for at least 30 min. Layers partitioned and the aqueous phase was extracted with THF (2×5.0 L). The combined organic layers were filtered with 0.22 um filter. The solution was concentrated to 5.0 L under vacuum at no more than 40° C. MeCN (5.0 L) was charged and the mixture was concentrated to 5.0 L at NMT 40° C. Additional MeCN (5.0 L) was charged and the mixture was concentrated to 3.0 L at NMT 40° C. Water (10.0 L) was added dropwise into the solution and the slurry was agitated for at least 0.5 h. The slurry was filtered and the cake was washed with MeCN: H2O=1:3 (2.0 L), followed by MTBE (2.0 L). The solid was dried in an oven under vacuum to give an off-white solid (0.61 kg, 87%)

Examples 19-26 show large scale synthesis of the steps shown in Examples 1-18.

Example 19

Synthesis of Compound 3

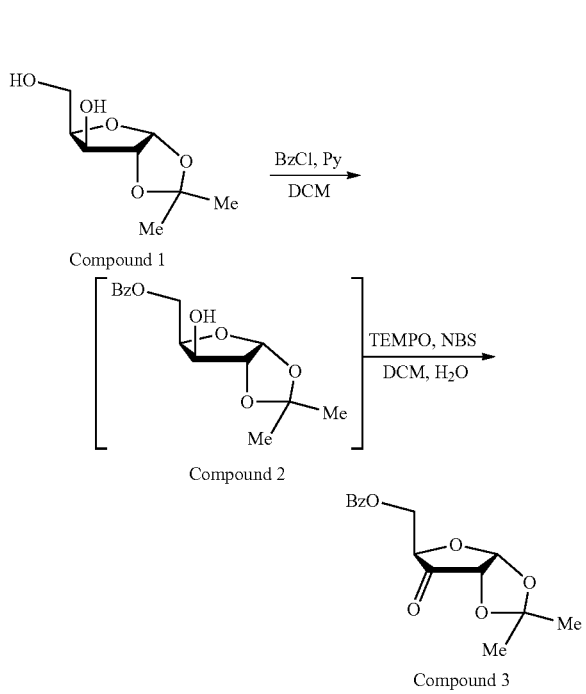

To a 50 L reactor under nitrogen protection was charged DCM (133 L, 6 L/kg) and the temperature was adjusted to 0° C. 1,2-O-Isopropylidene-α-D-xylofuranose (compound 1) (2.66 kg, LR) was charged to the reactor and stirred to dissolve. The solution was further cooled to −10° C. To the solution was added BzCl (1.56 kg, 1.05 eq) dropwise. The reaction was aged for 30 min and quenched with water (6.0 L, 3.0 eq.). The organic layer was washed with 20% (w/w) aqueous citric acid (8 L) twice, followed by 4% (w/w) NaHCO$_3$ (8 L) and 8% NaCl (w/w) solution (5 L). To the isolated organic layer was added DCM (8 L) and water (5 L). The mixture was cooled to 0-10° C. Solid NaHCO$_3$ (1.35 kg, 1.0 eq) was charged and TEMPO (0.202 kg, 0.05 eq.) was charged to the reactor. Next NBS (2.54 kg, 0.9 eq) was charged portion-wise while maintaining temperature at 0-10° C. The mixture was stirred for at least 2 hours. The reaction was quenched with 8% (w/w) Na$_2$SO$_3$ (5.0 kg, 1 L/kg) and the aqueous phase was back extracted with DCM (12.2 kg, 2 L/kg) once. The combined organic layer was washed with 8% (w/w) aqueous NaCl solution (10 kg, 2 L/kg) and solvent swapped to MTBE. To the MTBE solution at 45° C. heptane (12.96 kg, 4 L/kg) was added dropwise. The solution was cooled to 20° C. and held for 3 h. The slurry was filtered and dried to give off-white solid (2.96 kg, 61%).

Data for Compound 3: $^1$H NMR (400 MHz, CHLOROFORM-d) δ 7.93 (d, J=7.7 Hz, 2H), 7.55 (t, J=7.2 Hz, 1H), 7.42 (t, J=7.7 Hz, 2H), 6.12 (d, J=4.4 Hz, 1H), 4.70-4.65 (m, 2H), 4.48-4.39 (m, 2H), 1.49 (s, 3H), 1.41 (s, 3H);

$^{13}$C NMR (101 MHz, CHLOROFORM-d) δ 207.6, 165.7, 133.3, 129.4, 129.2, 128.4, 114.3, 103.0, 76.1, 63.3, 27.3, 26.9;

LCMS [M+H] calcd for C$_{15}$H$_{17}$O$_6$=293.1; found=293.0.

Example 20

Synthesis of Compound 8

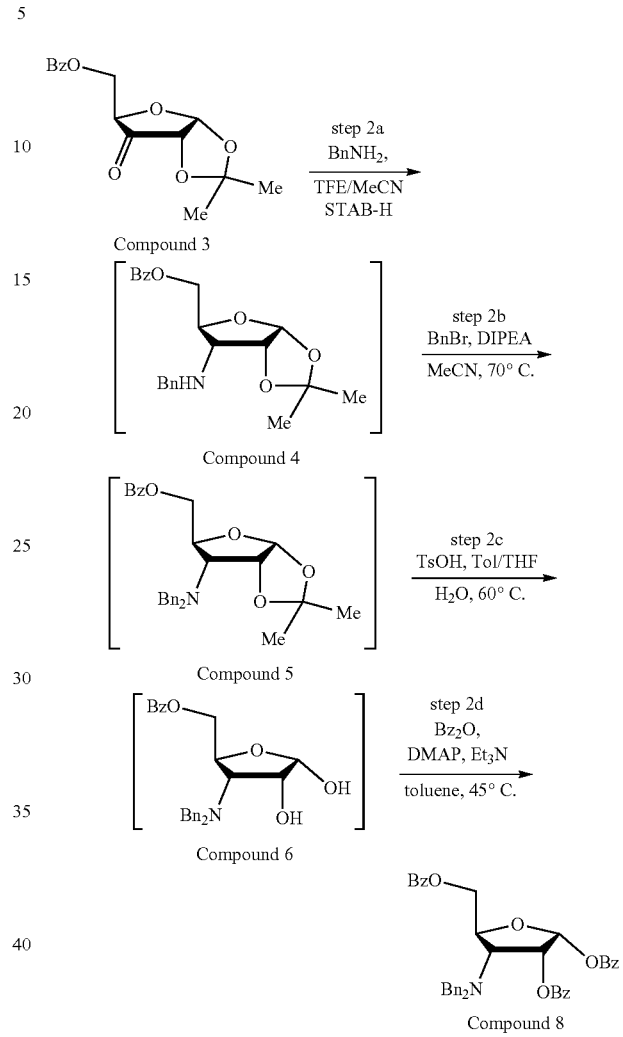

To a 20 L reactor under nitrogen protection was charged MeCN (6.97 kg, 5 L/kg), TFE (2.40 kg, 1 L/kg) and Compound 3 (2.40 kg, 1 eq.). The temperature was adjusted to 8° C. and BnNH2 (0.790 kg, 1.2 eq) was added to the reactor over 60 min. To a separate 50 L reactor, MeCN (7.12 kg, 5 L/kg) and NaBH(OAc)$_3$ (3.92 kg, 3.0 eq) were charged and stirred at 7° C. to form a white suspension for the reverse quench. After 16 h, the imine solution of compound 3 was transferred to the suspension over 60 min. After 1 h, the solution was quenched with aqueous 8% (w/w) citric acid and 5% (w/w) NaCl solution (10.16 kg, 5 L/kg). The organic layer was separated and washed with 15% (w/w) Na$_2$CO$_3$ solution (10 kg, 5 L/kg), 6% (w/w) NaHCO$_3$ solution (4.5 kg, 3 L/kg) and 20% (w/w) NaCl solution (5.4 kg, 3 L/kg). The organic layer was isolated and azeodried in MeCN. In a 50 L reactor, the solution of Compound 4 (2.57 kg, 1 eq) in MeCN (5.1 L, 2.0 L/kg) was charged and DIEA (2.62 kg, 3.0 eq.) was added followed by BnBr (2.29 kg, 2.0 eq). The solution was heated to 70° C. and aged for 7 h. The solution was cooled to 25° C. and Et$_3$N (0.67 kg, 1.0 eq) was added followed by dilution with toluene (11.1 kg, 5 L/kg). The solution was washed with 5% (w/w) citric acid solution (5 L) and 15% (w/w) NaCl solution (5 L). The organic solution was transferred back to 50 L reactor and THF (2.6 kg, 1 L/kg) was added followed by water (1.5 kg, 0.5 L/kg). TsOH H₂O (2.38 kg, 2.0 eq.) was added to the solution and the solution was heated to 60° C. for 1 h. The solution was cooled and toluene (12.8 kg, 5 L/kg) was added to give a phase split. The organic layer was washed with 7% (w/w) NaHCO₃ solution (19.5 kg, 6 L/kg) to reach pH greater than 7. The organic phase was isolated and washed with 20% (w/w) aqueous NaCl solution (7.5 kg, 2 L/kg) and separated. To the org solution was added DMAP (0.036 kg, 0.05 eq), Et3N (1.79 kg, 3.0 eq) and Bz₂O (2.98 kg, 2.2 eq). The solution was stirred at 45° C. for 6 h and cooled to RT. To the solution was added THF (11.0 kg, 5 L/kg). The organic was then washed with 20% (w/w) NaCl solution (7.5 kg, 2 L/kg). The solution was solvent-swapped to 2MeTHF and heptane was added to initiate crystallization. The slurry was stirred at 20° C. for 3 h and filtered and dried to give light-brown solid (2.55 kg, 67%).

Data for Compound 8:
¹H NMR (400 MHz, CHLOROFORM-d) δ 8.20 (d, J=7.6 Hz, 2H), 7.81 (d, J=7.7 Hz, 2H), 7.75-7.53 (m, 6H), 7.48-7.36 (m, 7H), 7.28 (t, J=7.5 Hz, 4H), 7.23-7.10 (m, 4H), 6.50 (s, 1H), 5.92 (d, J=4.2 Hz, 1H), 4.98 (brd, J=9.8 Hz, 1H), 4.76 (dd, J=12.3, 2.0 Hz, 1H), 4.49 (dd, J=12.3, 3.7 Hz, 1H), 4.22 (d, J=13.6 Hz, 2H), 4.05 (dd, J=9.8, 4.1 Hz, 1H), 3.77 (d, J=13.6 Hz, 2H);
¹³C NMR (101 MHz, CHLOROFORM-d) δ 166.3, 165.7, 164.5, 138.9, 133.9, 133.4, 132.8, 130.0, 129.9, 129.5, 129.3, 129.3, 128.6 (t, J=18.3 Hz, 1C), 128.1, 128.5 (t, J=115.5 Hz, 1C), 98.9, 74.8, 63.4, 58.2, 55.9;
LCMS [M+H] calcd for C₄₀H₃₆NO₇ 642.7; found=624.8.

Example 21

Synthesis of Compound 10

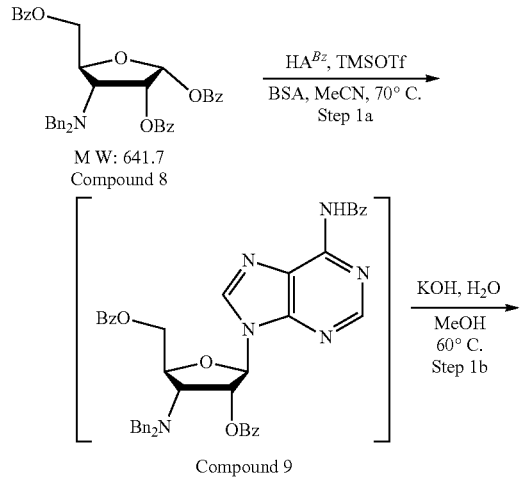

MeCN (0.8 L, 8.0 L/kg) was charged to an inert reactor and agitation was started. Compound 8 (0.10 kg, LR), HA$^{Bz}$ (39.1 g, 1.05 eq) and BSA (38.1 g, 1.2 eq) were charged, into the reactor. The reaction mixture was heated to 70-75° C. and stirred until a clear solution was obtained. TMSOTf (34.6 g, 1.0 eq.) was added drop-wise into the reactor at 65-75° C. The reaction mixture was stirred for 4 h at 65-75° C. and then cooled 15-25° C. 5% (w/w) aqueous NaHCO₃ (0.2 L, 2 L/kg) and i-PrOAc (1 L, 10 L/kg) were charged into the mixture which was stirred for at least 30 mins at 10-30° C. The organic phase and water phase were separated. i-PrOAc (1 L, 10 L/kg) was charged into the water phase and stirred for at least 30 mins for back extraction. The organic phases were combined and 5% (w/w) aqueous NaHCO₃ (0.2 L, 2 L/kg) was charged into the organic phase and stirred at 10-30° C. The organic phase was washed with 15% (w/w) aqueous brine (0.5 L/kg). The separated organic phase is concentrated under vacuum and solvent exchanged to MeCN. To the crude, MeOH (3 L/kg) and dropwise aq 5% (w/w) KOH solution (0.1 L, 1 L/kg) was charged into the mixture. The mixture is stirred for at least 5 hours at 55-65° C. The reaction mixture was cooled to 0-5° C. and then water (1.5 L, 15 L/kg) was added dropwise into the mixture over at least 1 hour at 0-25° C. The slurry was filtered and the cake was washed with water (0.2 L, 2 L/kg). The product cake (47.9 g, 69%) was collected as an off-white solid.

Data for Compound 10:
¹H NMR (400 MHz, DMSO-d₆) δ 8.20 (s, 1H), 8.06 (s, 1H), 7.40 (d, J=7.5 Hz, 3H), 7.35-7.28 (m, 5H), 7.26-7.18 (m, 2H), 6.02 (d, J=4.8 Hz, 1H), 5.88 (br s, 1H), 5.41-5.30 (m, 1H), 4.73 (br t, J=5.6 Hz, 1H), 4.43 (br s, 1H), 4.03 (d, J=14.1 Hz, 2H), 3.89 (br d, J=14.1 Hz, 2H), 3.74 (br d, J=11.6 Hz, 1H), 3.55-3.40 (m, 2H);
¹³C NMR (101 MHz, DMSO-d₆) δ 156.6, 152.7, 149.2, 140.6, 140.0, 128.8, 128.6, 127.2, 119.7, 91.0, 82.2, 75.4, 63.0, 59.5, 55.3;
LCMS [M+H] calcd for C₂₄H₂₇N₆O₃ 447.5; found=447.2.

Example 22

Synthesis of Compounds 15 and 16

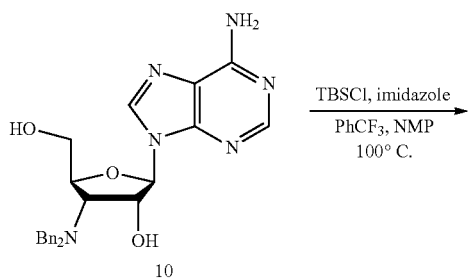

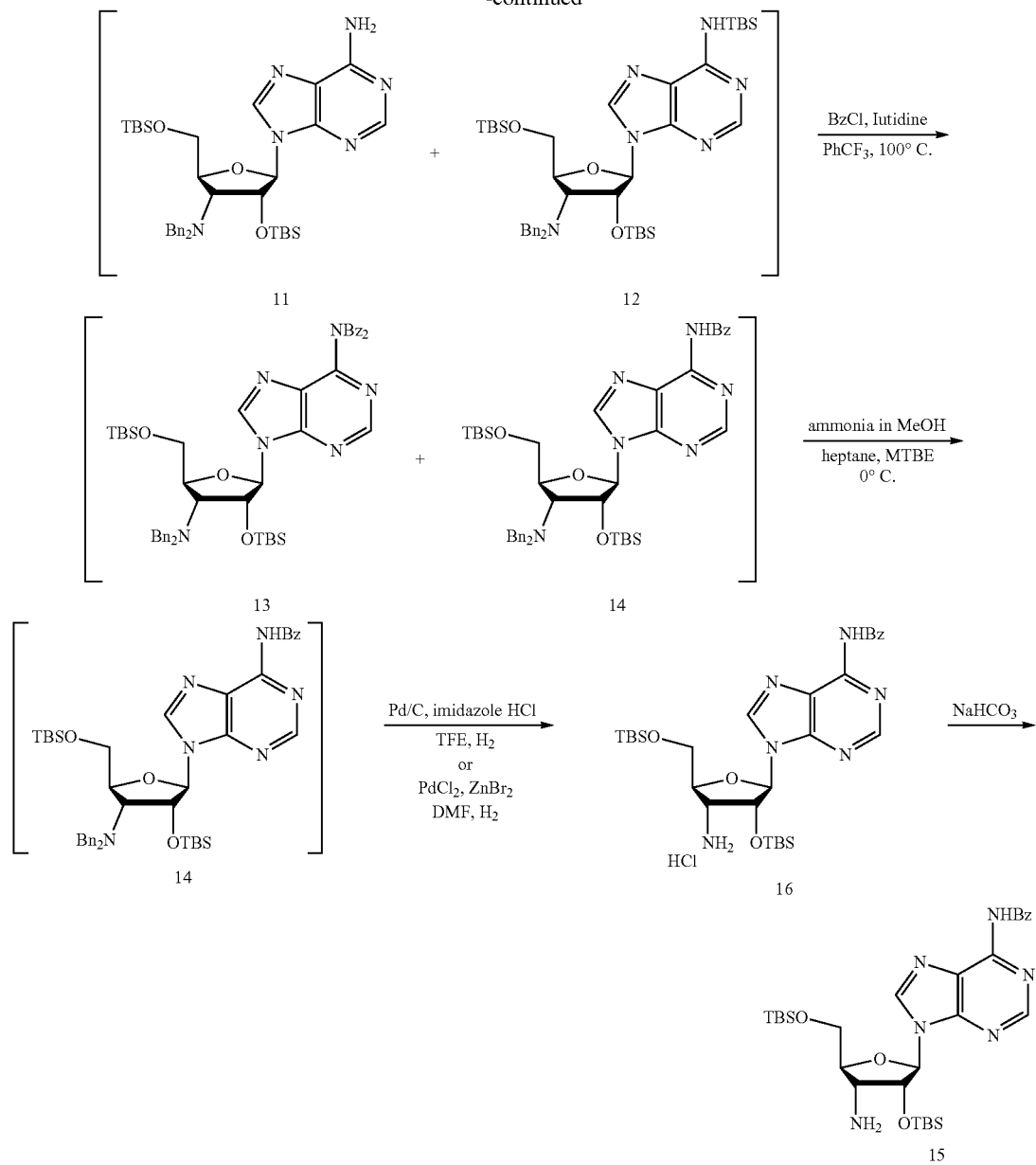

To an inert reactor was charged CF₃Ph (750 mL, 5 L/kg) and Compound 10, (150 g), NMP (150 mL, 1 L/kg) and imidazole (229 g, 10 eq). TBSCl (203 g, 4 eq.) was charged to the solution portion wise and the solution was heated to 100° C. for 16 h. The reaction mixture was cooled to 20-40° C. MeOH (375 mL, 2.5 L/kg) was charged to the reactor and aged for 30 min at 20-40° C. H₂O (375 mL, 2.5 L/kg) and n-heptane (750 mL, 5 L/kg) were added into the mixture and aged for 30 min. Separate the layers were separated and the separated aqueous phase was back extracted with n-heptane (375 mL, 2.5 L/kg) and the organic phases were combined. To the organic phase, celite (kg/kg) and 15% (w/w) aqueous brine (750 mL, 5 L/kg) were added. The mixture was filtered and the organic phase was separated. The organic phase was solvent swapped to PhCF3 and concentrated to 2 L/kg.

CF₃Ph (1.2 L, 8 L/kg) was charged to the solution. 2,6-lutidine (144 g, 4 eq.) was added and the solution was heated to 85° C. BzCl (118 g, 2.5 eq.) was added to the solution dropwise and the reaction was held for 3 h. The reaction mixture was cooled to 25° C., 5% (w/w) aqueous NaHCO₃ (1.5 L, 10 L/kg) and MTBE (1.5 L, 10 L/kg) were charged to the reaction mixture and stirred. The organic phase was separated and washed with 15% (w/w) aqueous brine (1.5 L, 10 L/kg). The isolated organic phase was concentrated and solvent-swapped to heptane at 5 L/kg.

To the heptane solution, MTBE (1.2 L, 8 L/kg) and n-heptane (900 mL, 6 L/kg) were charged. 7 M NH₃/MeOH (112 g, 3 eq.) was charged at 0° C. and the reaction was held for 7 h. 10% (w/w) aqueous citric acid (1.5 L, 10 L/kg) and celite (1% kg/kg) were charged into the mixture at 0° C. The mixture was filtered and the organic phase was separated. The organic phase was washed with aqueous 15% brine (1.5 L, 10 L/kg). The separated organic phase was solvent swapped to TFE at 5 L/kg.

TFE (750 mL. 5 L/kg), Pd/C (Escat 1951, 15% w/w, 0.13 kg/kg) and Imidazole HCl (35.1 g, 1 eq.) were charged to the concentrate. The reactor was pressurized with $H_2$ at 2.5 bar and aged for 16 h at 45° C. The reaction mixture was cooled to 25° C. and celite (1 kg/kg) was added. The suspension was filtered and the cake was washed with TFE (300 mL, 2 L/kg). Imidazole HCl (17.5 g, 0.5 eq) was charged into the solution and which was concentrated to 2 L/kg. To the concentrate was charged IPA (1.5 L, 10 L/kg) at 0-10° C. and the reaction mixture was stirred for at least 1 hour at 0° C. The slurry was filtered after 1 h and the cake washed with IPA (1.5 L, 10 L/kg) and then IPA/$H_2O$ (900 mL, 5 L/kg, V:V=1:1). The cake was transferred to a reactor and MTBE (1.5 L, 10 L/kg) was added. aq. 5% (w/w) $NaHCO_3$ (3.0 L, 20 L/kg) was charged at 25° C. and aged for 2 h. To the mixture was added celite (1 kg/kg) and filtered after 30 min. The organic phase was washed with aqueous 15% (w/w) brine (1.5 L, 10 L/kg) at 25° C. and separated. The organic phase was treated with active carbon (10% kg/kg) at 25° C. for 18 h. The mixture was filtered through celite (1 kg/kg), and concentrated to 5 L/kg. To the solution was added n-heptane (3.0 L, 20 L/kg) over 30 min at 25° C. The slurry was aged for 2 h and the cake was filtered and washed with MTBE: n-heptane (300 mL, 2 L/kg, V:V=1:4) to give an off-white solid (147 g, 69%) after drying.

Data for Compound 16:

$^1$H NMR (400 MHz, DMSO-$d_6$) δ 11.26 (brs, 1H), 8.90-8.70 (m, 3H), 8.62 (s, 1H), 8.05 (d, J=7.5 Hz, 2H), 7.67-7.63 (m, 1H), 7.57-7.53 (m, 2H), 6.31 (d, J=5.1 Hz, 1H), 5.03 (t, J=5.7 Hz, 1H), 4.41 (br d, J=2.2 Hz, 1H), 4.10-4.00 (m, 1H), 3.99-3.88 (m, 2H), 0.87 (s, 9H), 0.76 (s, 9H), 0.06 (s, 6H), 0.03 (s, 3H), −0.23 (s, 3H);

$^{13}$C NMR (101 MHz, DMSO-$d_6$) δ 165.6, 152.1, 151.9, 150.7, 142.1, 133.2, 132.5, 128.5, 128.4, 125.4, 87.6, 81.5, 74.2, 63.0, 51.1, 25.8, 25.6, 18.0, 17.6, −5.0, −5.4, −5.4;

LCMS [M+H] calcd for $C_{29}H_{47}N_6O_4Si_2$ (free form)=599.9; found=600.1.

Data for Compound 15:

$^1$H NMR (400 MHz, CHLOROFORM-d) δ 9.12 (s, 1H), 8.80 (s, 1H), 8.56 (s, 1H), 8.02 (d, J=7.5 Hz, 2H), 7.62-7.49 (m, 3H), 6.11 (s, 1H), 4.40 (d, J=4.3 Hz, 1H), 4.11 (dd, J=11.5, 2.1 Hz, 1H), 3.98-3.89 (m, 2H), 3.61 (dd, J=8.3, 4.6 Hz, 1H), 1.60 (brs, 2H), 0.95 (s, 18H), 0.79 (s, 1H), 0.22 (s, 3H), 0.15 (s, 3H), 0.14 (s, 3H), 0.13 (s, 3H);

$^{13}$C NMR (101 MHz, CHLOROFORM-d) δ 164.6, 152.6, 151.0, 149.3, 141.6, 133.9, 132.7, 128.8, 127.8, 123.2, 90.0, 85.1, 77.9, 61.9, 52.2, 26.1, 25.8, 18.6, 18.1, −4.4, −4.9, −5.3, −5.4;

LCMS [M+H] calcd for $C_{29}H_{47}N_6O_4Si_2$ (free form)=599.9; found=599.9.

Example 23

Synthesis of Compound 17

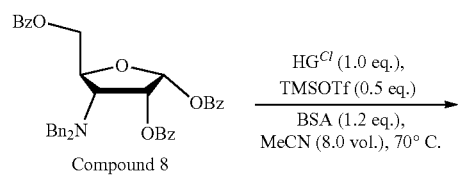

Compound 8

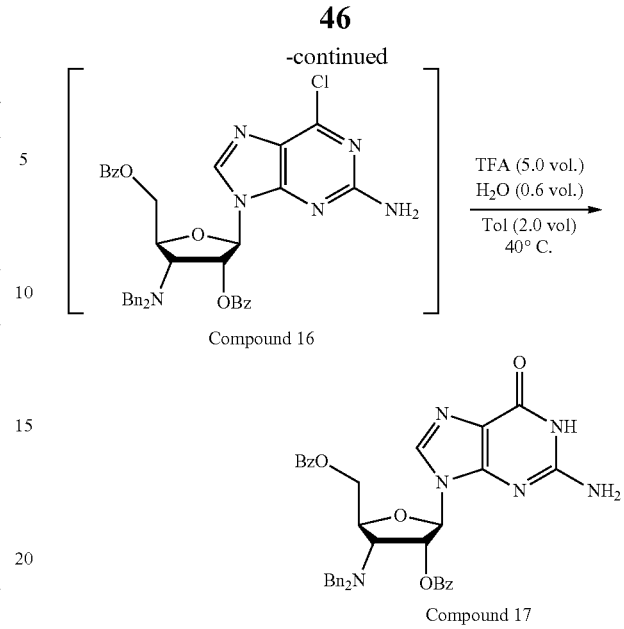

Vorbruggen Reaction

MeCN (8 L) and Compound 8 (1.0 kg, LR) were charged into a reactor and stirred to make a solution. 2-Amino-6-chloropurine (0.26 kg, 1.0 eq.) and BSA (0.38 kg, 1.2 eq.) were charged into the reaction mixture. The suspension was heated at 75-85° C. Then, TMSOTf (0.18 kg, 0.5 eq.) was charged into the solution at 70-75° C. and the reaction was aged for 4 h until completion;

The reaction was cooled to 25° C. and quenched with $NaHCO_3$ (5.0 L, 5% wt, aq.). To the mixture, toluene (2.0 L) was added to extract product and organic layer was separated. The organic layer was washed with $NaHCO_3$ (5.0 L, 5% wt) followed by brine (5 L, 15%). The organic layer was concentrated and solvent swapped to toluene to a final volume of 1.5-2.0 L/kg. The solution was used in next step without isolation.

Hydrolysis

To the above solution, $H_2O$ (0.6 V) was charged into the reactor. Next, TFA (5.0 V) was charged into the reactor. The jacket was heated to 35-45° C. and the solution was stirred for at least 20 h at 40° C. The reaction mixture was cooled to 10° C. and $H_2O$ (10.0 V) was charged into the mixture at 25° C. The organic phase and water phase were separated. To the aqueous phase, toluene (4.0 V) was charged and the solution was stirred for at least 30 minutes at 15° C. The organic phase was separated and all organic phases were combined and washed with water (10.0 V). The organic phase was then washed with 15% (w/w) $K_3PO_4$ (3 L). The organic phase was polish filtered and washed with 15% (w/w) brine (aq. 4 V). The organic phase was concentrated to 2.5-3.0 V under vacuum at NMT 60° C. The concentrated solution was then added over 2-3 h to heptane (10.0 V) at 35-45° C. for crystallization. The solids were filtered and washed with heptane (2.0 V); wet cake was dried at 35-45° C. to give light brown solids. (825 g, 79%).

Data for Compound 17

$^1$H NMR (600 MHz, DMSO-$d_6$, 25° C.): δ 10.84 (v br s, 1H), 8.11 (br d, J=7.8 Hz, 2H), 7.77 (br d, J=7.8 Hz, 2H), 7.72 (br t, J=7.4 Hz, 1H), 7.65 (s, 1H), 7.65 (t, J=7.4 Hz, 1H), 7.59 (t, J=7.7 Hz, 2H), 7.47 (t, J=7.7 Hz, 2H), 7.29 (br d, J=7.6 Hz, 4H), 7.19 (br t, J=7.6 Hz, 4H), 7.13 (br t, J=7.2 Hz, 2H), 6.16 (overlapped, 2H), 5.00 (m, 1H), 4.73 (dd, J=12.2, 2.7 Hz, 1H), 4.51 (dd, J=12.2, 4.8 Hz, 1H), 4.16 (dd, J=8.3, 5.9 Hz, 1H), 4.05 (d, J=14.2 Hz, 2H), 3.86 (d, J=14.2 Hz, 2H).

$^{13}$C NMR (151 MHz, DMSO-d$_6$, 25° C.): δ 165.5, 165.0, 156.7, 153.7, 150.6, 139.1, 135.7, 133.9, 133.4, 129.6, 129.2, 129.2, 128.9, 128.9, 128.6, 128.2, 128.2, 127.0, 117.0, 87.2, 76.3, 75.2, 63.8, 59.2, 54.8.

HRMS (ESI) Calcd for [C$_{38}$H$_{34}$N$_6$O$_6$+H]$^+$671.2613, Found 671.2597

Example 24

Synthesis of Compound 18

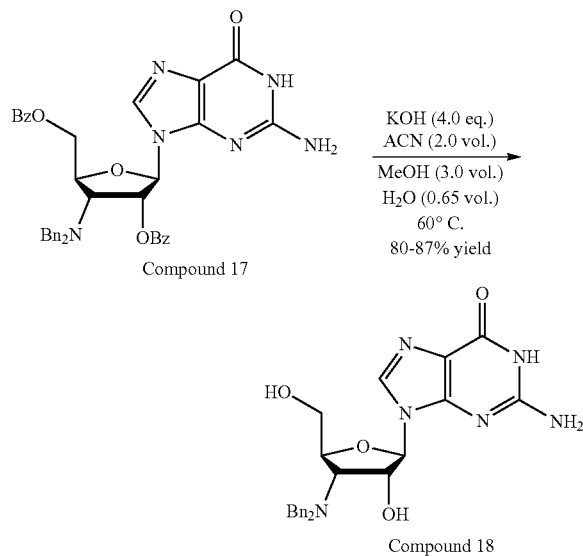

To the reaction was charged MeCN (2.0 L/kg, 2 vol) and MeOH (3.0 L/kg, 3 vol). The reaction mixture was agitated and Compound 17 (1.0 kg, LR) was charged into the reactor. Next, the KOH solution (0.65 L/kg, 4.0 eq KOH) was charged into the reactor at 25-35° C. The solution was heated to 55-65° C. for 2 h.

The reaction mixture was cooled to 15-25° C. and 1 N aq. HCl (1.0-2.0 L/kg, 1.0-2.0 vol) was added to the reactor to adjust the pH to 7-8 at 20° C. The slurry was aged for 30 min and solids were filtered; cake was washed with water (2 L) and MeCN/MeOH (v/v=1/1) until benzoic acid AP is less than 20%.

The cake was transferred to a reactor and 5% (w/w) Na$_2$CO$_3$ (10.0 vol) was charged into the reactor. The slurry was agitated at 65-75° C. for 3 h and the mixture was cooled to 15-25° C., and then agitated for no less than 1 h. The solid was filtered and the cake washed with water until benzoic acid AP is less than 4.5%; cake was dried in a vacuum oven at 45-55° C. until KF is less than 2%.

The dry cake and NMP (4.0 vol) were charged into another reactor and the mixture heated at 60-70° C. for no less than 20 min. The solution was cooled to 40-50° C. and the pH adjusted to 7 with AcOH. The solution was cooled to 15-25° C. and agitated for no less than 1 h. MTBE (15 L/kg) was added slowly to the reactor and the slurry was agitated for no less than 2 h at 15-25° C. The solids were filtered and the cake was washed with MTBE (2.0 L/kg, 2.0 vol). The cake was dried in a vacuum oven at 45-55° C. until KF<0.5% to give a light brown solid (0.6 kg, 87%).

Data for Compound 18

$^1$H NMR (600 MHz, DMSO-d$_6$, 25° C.): δ 7.70 (s, 1H), 7.40 (br d, J=7.6 Hz, 4H), 7.31 (br t, J=7.5 Hz, 4H), 7.22 (br t, J=7.4 Hz, 2H), 5.82 (d, J=5.3 Hz, 1H), 4.61 (m, 1H), 4.36 (m, 1H), 4.01 (d, J=14.1 Hz, 2H), 3.85 (d, J=14.1 Hz, 2H), 3.66 (dd, J=11.5, 1.7 Hz, 1H), 3.43 (dd, J=11.6, 3.7 Hz, 1H), 3.40 (m, 1H).

$^{13}$C NMR (151 MHz, DMSO-d$_6$, 25° C.): δ 158.2, 154.9, 151.0, 140.1, 134.8, 128.3, 128.1, 126.8, 116.7, 89.1, 81.3, 75.0, 62.6, 59.2, 54.7.

HRMS (ESI) Calcd for [C$_{24}$H$_{26}$N$_6$O$_4$+H]$^+$463.2088, Found 463.2070 (4.0 ppm error).

Example 25

Synthesis of Compound 21

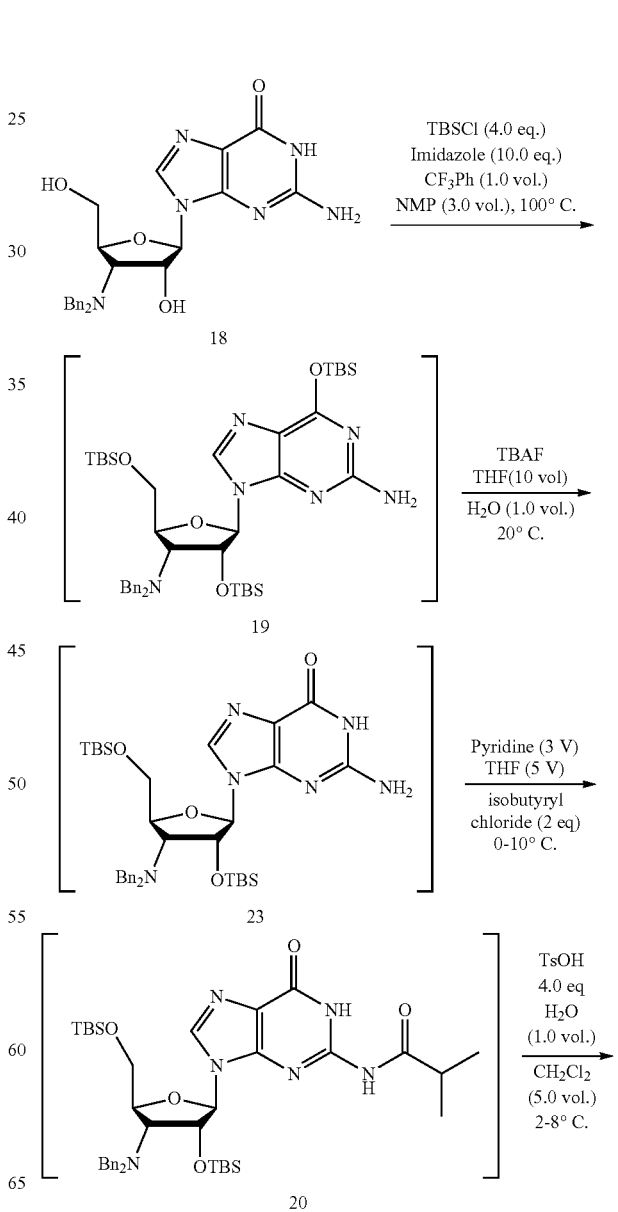

-continued

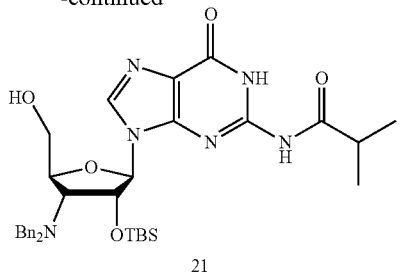

21

NMP (3.0 L/kg), Compound 18 (1.0 kg, LR), and imidazole (1.47 kg, 10.0 eq.) were charged to the reactor and agitated for 30 min. The reaction mixture was heated to 55-65° C. and the solution of TBSCl (1.3 kg/kg, 4.0 eq.) in CF$_3$Ph (1.0 L/kg) was charged to the reactor. The solution was stirred for no less than 8 h at 95-105° C. The reaction mixture was cooled to 15-25° C. MTBE (10.0 L/kg, 10.0 vol) and MeOH (1.0 L/kg, 1.0 vol) were charged into the reactor and agitated for 30 min. Then 10% (w/w) citric acid (8.0 L/kg) was charged into the reactor for no less than 30 min. The phases were separated and the organic phase was retained. The organic was washed with water (5.0 kg/L, 5.0 vol) and the aqueous and organic phase were separated; the organic phase was retained. The batch was concentrated at 60° C. under vacuum to 3 L/kg. To the crude stream was added THF (5 L/kg, vol) and the batch was concentrated under vacuum to 2.0 L/kg. This stream will be used directly in next step.

The above 2 L stream, THF (8 L/kg), and water (1 L/kg) were charged to a reactor. TBAF (1.0 eq, based on actual tri-TBS intermediate amount) was charged and the reaction was aged at 20° C. for 2 h. Heptane (10 L/kg) and 15% NH4Cl (5 L/kg) were charged to the reaction and the mixture was stirred and the aqueous layer was separated. The organic layer was washed with 15% brine (5 L/kg); concentrated and solvent swapped into THF at 55° C. under vacuum. The final THF solution is 2 vol and was used directly in the next step.

Under N$_2$, the THF solution (2V) and pyridine (3V) were charged to the reactor and the mixture was cooled to 0-10° C. 2.0 eq. isobutyryl chloride was charged into the mixture under 0-10° C. The solution was warmed to 10-20° C. and aged for 1 h; after reaction completion, 3V THF was charged to the reaction system. The reaction system was cooled to 0-10° C. 2-3% NH$_3$·H$_2$O (1.0 kg/kg)) was charged slowly to the reaction mixture at 0-10° C. and the reaction was continued until no di iBu protected intermediate was observed. MTBE (8.0 L) and 30% citric acid (8.0 L) were charged to the mixture. The aqueous layer was separated and organic layer was washed with 30% citric acid (8 L/kg). The aqueous layers was separated and organic layer was washed with 5% NaHCO$_3$ (5 L/kg) and 20% NaCl (5 L/kg). The organic layer was separated, concentrated to 2 vol, and used directly in next step.

Above 2 vol organic stream was charged to a reactor. DCM (8.0 L) and water (1.0 L) were added to the reaction. The solution was maintained at 2-8° C., and TsOH (4.0 eq.) was charged to the mixture, which was agitated for 8 h. DIPEA was added slowly to the mixture at 0-10° C., to adjust the pH to 7-8. The reaction temperature was increased to 20° C. Water (10 L) was added and the organic phase was separated. The organic phase was washed with water (10 L). The organic layer was concentrated and solvent swapped at 45° C. into iPrOH to the final volume of 6 L. The slurry was aged at 50-60° C. for 2-3 hr and cooled to 2-8° C. and aged for 1 h before filtration. (1.1 kg, 76%).

Data for Compound 21

$^1$H NMR (600 MHz, DMSO-d$_6$, 25° C.): δ 12.09 (br s, 1H), 11.56 (s, 1H), 8.25 (s, 1H), 7.42 (br d, J=7.7 Hz, 4H), 7.33 (br t, J=7.6 Hz, 4H), 7.25 (br t, J=7.4 Hz, 2H), 6.02 (d, J=6.8 Hz, 1H), 5.14 (t, J=5.0 Hz, 1H), 4.85 (br t, J=7.4 Hz, 1H), 4.53 (m, 1H), 4.33 (d, J=4.2 Hz, 1H), 3.96 (d, J=13.6 Hz, 2H), 3.75 (d, J=13.6 Hz, 2H), 3.66 (m, 1H), 3.50 (dt, J=11.6, 4.3 Hz, 1H), 3.44 (dd, J=7.9, 3.1 Hz, 1H), 2.74 (sept, J=6.9 Hz, 1H), 1.09 (br d, J=6.9 Hz, 6H), 0.79 (s, 9H), 0.01 (s, 3H), −0.41 (s, 3H).

$^{13}$C NMR (151 MHz, DMSO-d$_6$, 25° C.): δ 180.1, 154.7, 149.0, 148.2, 139.4, 137.4, 128.5, 128.2, 127.0, 119.8, 88.8, 81.8, 77.2, 63.0, 60.1, 54.1, 34.7, 25.5, 18.8, 18.7, 17.5, −4.8, −5.9.

HRMS (ESI) Calcd for [C$_{34}$H$_{46}$N$_6$O$_5$Si+H]$^+$647.3372, Found 647.3347 (3.8 ppm error).

Example 26

Synthesis of Compound 22

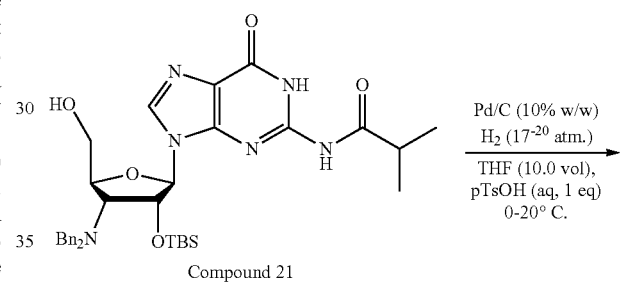

Compound 21

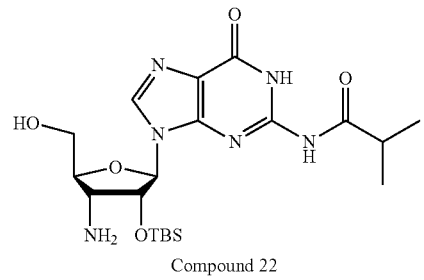

Compound 22

The reactor was inerted with nitrogen and THF (10 L), Compound 21 (1.0 kg, LR), and 10% Pd/C (0.1 kg) were charged to the reactor. The reaction was cooled to 0° C. and TsOH·H2O (0.28 kg, 1.0 eq.) in water (1 L) was charged. The reactor was backfilled with H$_2$ five times. The H2 pressure was adjusted to 1.7 to 2.0 MPa and reaction was aged for 6 h at 5-10° C. until Compound 21<0.8 AP; the temperature was adjusted to 20° C. and aged until the starting material and mono-Bn intermediate<0.5 AP;

The reactor was purged with N2 eight times. The mixture was filtered (through diatomite 1.0 w/w) and the cake washed with THF (2 L). DIPEA (1.1 eq), THF (15 L), and TMT-Na solution (1% TMTNa in 5 L 10% NaCl, w/w) were charged to the reaction solution. The solution was mixed and the layers separated. The aqueous layer was back extracted with THF; the combined organic layers were washed with 2% L-Cysteine in 20% brine (5 L) twice; and the organic layer was washed with 25% brine (5 L).

The organic layer was concentrated and solvent swapped into MeCN to 5 L. Water (10V) was charged into the solution and the slurry was stirred for at least 0.5 h. The solids were filtered and the cake washed with MeCN:H₂O=1:3 (3 L) and toluene (4 L). The cake was dried at 60-70° C. under vacuum to afford off-white solids (0.72 kg, 86%)

Data for Compound 22

¹H NMR (600 MHz, DMSO-d₆, 25° C.): δ 8.27 (s, 1H), 5.87 (d, J=4.6 Hz, 1H), 5.00 (br m, 1H), 4.48 (t, J=5.0 Hz, 1H), 3.77 (m, 1H), 3.68 (br d, J=11.8 Hz, 1H), 3.57 (br d, J=11.8 Hz, 1H), 3.50 (t, J=5.2 Hz, 1H), 2.79 (sept, J=6.9 Hz, 1H), 1.12 (d, J=6.9 Hz, 6H), 0.80 (s, 9H), −0.03 (s, 3H), −0.13 (s, 3H).

¹³C NMR (151 MHz, DMSO-d₆, 25° C.): δ 180.1, 154.8, 148.7, 148.1, 137.5, 120.0, 87.1, 86.1, 76.9, 61.4, 53.4, 34.7, 25.5, 18.9, 18.8, 17.7, −5.2, −5.3.

HRMS (ESI) Calcd for [C₂₀H₃₄N₆O₅Si+H]⁺467.2433, Found 467.2419 (3.0 ppm error).

We claim:

1. A process for preparing Compound 8 of the formula:

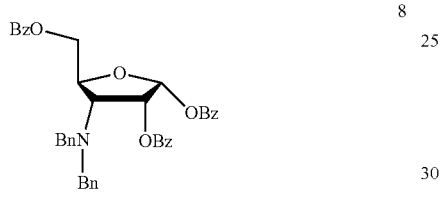

8 comprising the steps of a) reacting Compound 1 in a benzoyl protection reaction

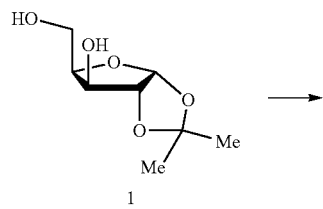

1

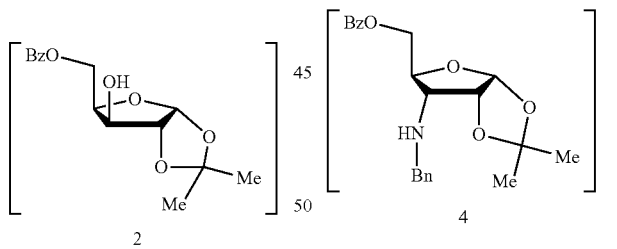

2 to afford Compound 2;

b) reacting Compound 2 in an oxidation reaction to afford Compound 3;

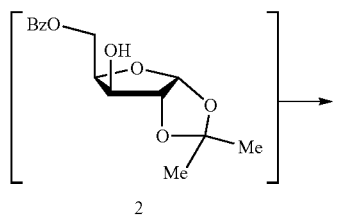

2

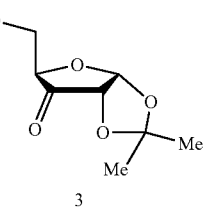

3 c) which is subsequently reacted in a reductive amination

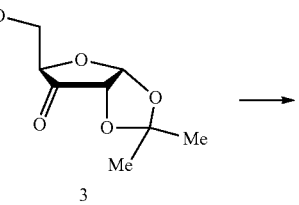

3

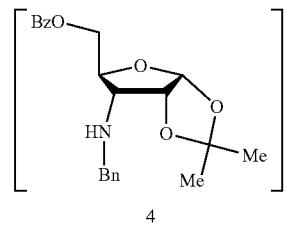

4 to afford Compound 4;

d) Compound 4 is reacted in a protection step using a benzyl protecting agent and base in a solvent at a temperature of about 70° C. to afford Compound 5 of the formula

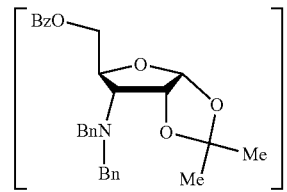

4

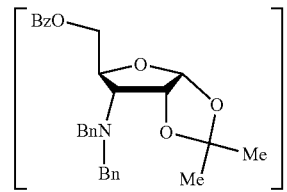

5 e) which is subsequently reacted in a deprotection step with an acid in a common organic solvent to afford Compounds 6 and 7 of the formula

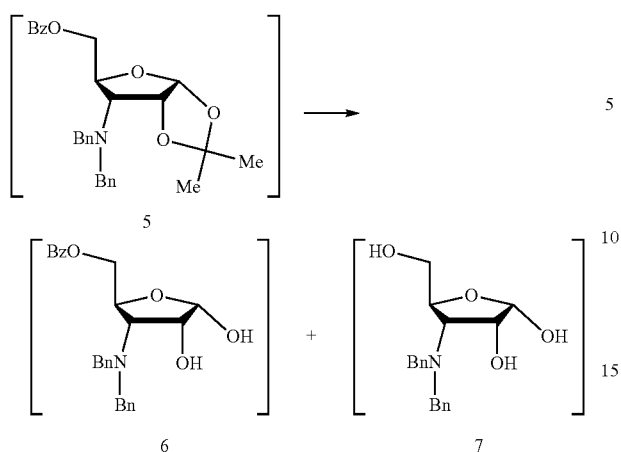

f) and reacting Compounds 6 and 7 with a benzoyl protecting reagent and a base in an organic solvent to afford Compound 8.

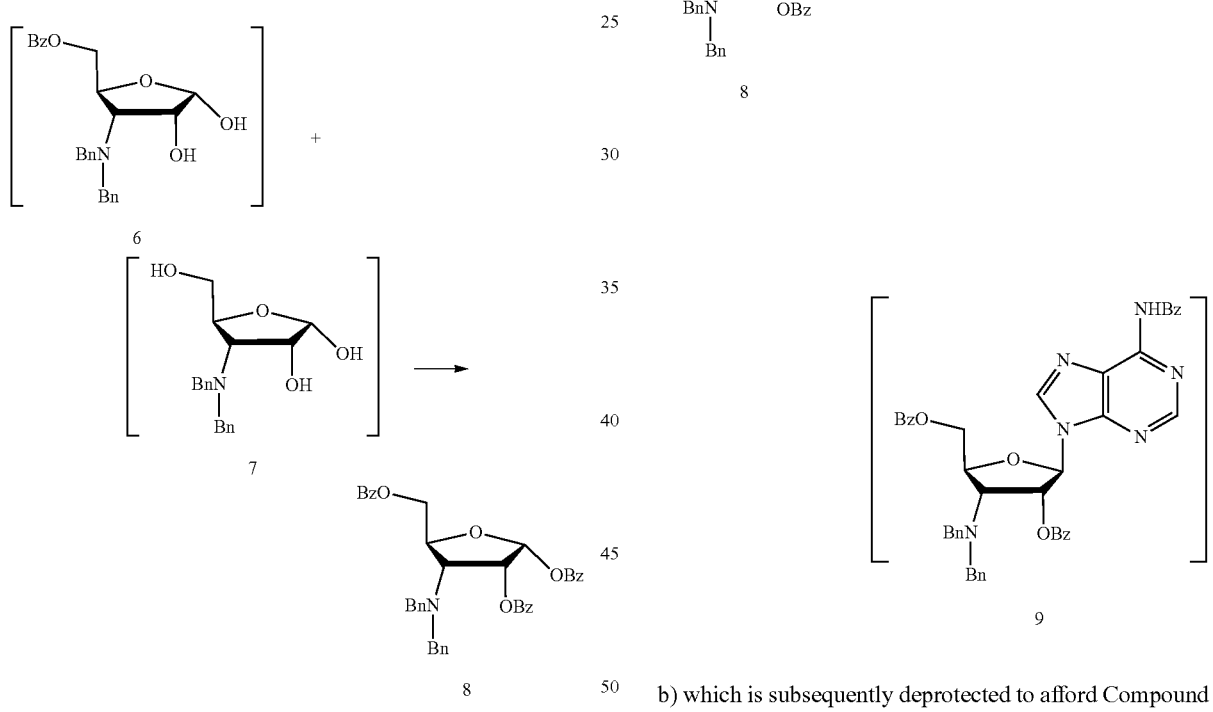

2. The process according to claim 1 wherein the protecting group in step a) is benzyl chloride.

3. The process according to claim 1 wherein the oxidation group in step b) is TEMPO.

4. The process according to claim 1 wherein the reducing group in step c) is $BnNH_2$.

5. The process according to claim 1 wherein the protecting group in step d) is BnBr.

6. The process according to claim 1 wherein the base in step d) is a Hunig's base.

7. The process according to claim 1 wherein the deprotecting agent in step e) is TsOH.

8. The process according to claim 1 wherein the protecting group in step f) is $Bz_2O$.

9. A process for preparing Compound 15 of the formula

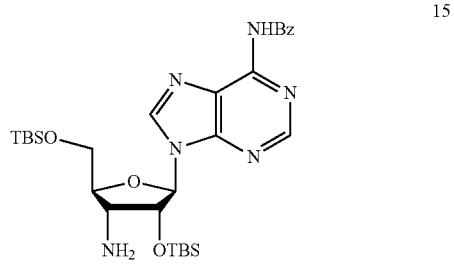

a) which comprises reacting Compound 8 using Vorbrüggen chemistry to afford Compound 9 b) which is subsequently deprotected to afford Compound 10 of the formula

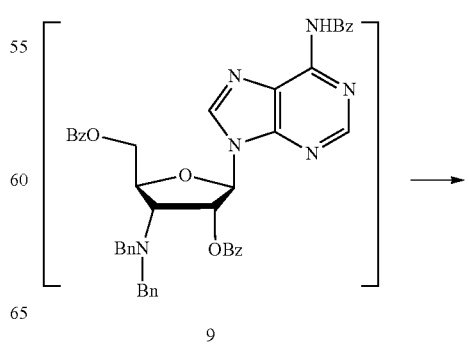

-continued
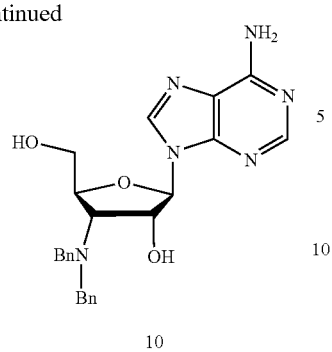
5
10
c) which is then subsequently protected to afford Compounds 11 and 12 of the formula
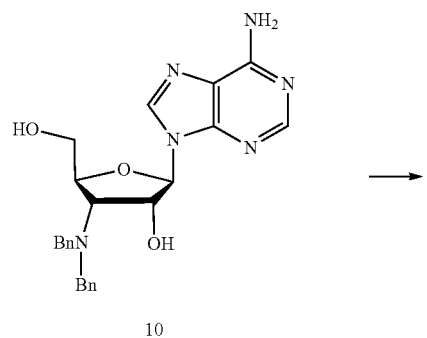
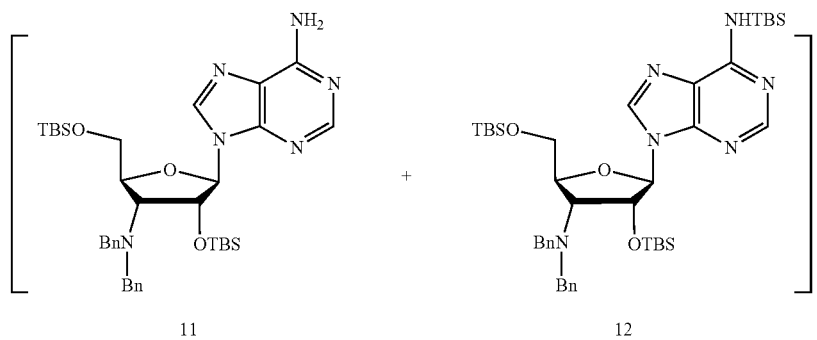
d) which are reacted with a benzoyl protecting reagent to afford Compound 13 of the formula
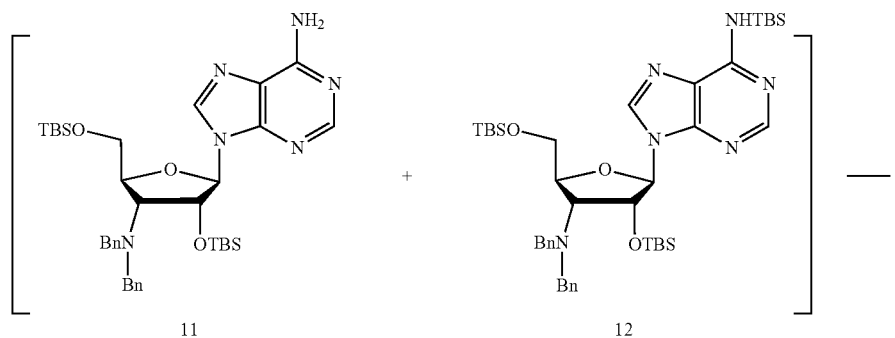

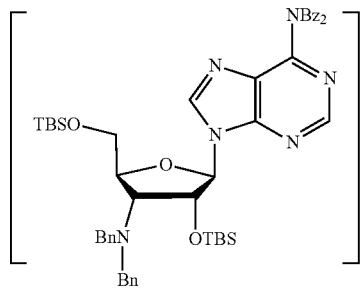

13 e) Compound 13 is then reacted with ammonia to afford Compound 14 of the formula

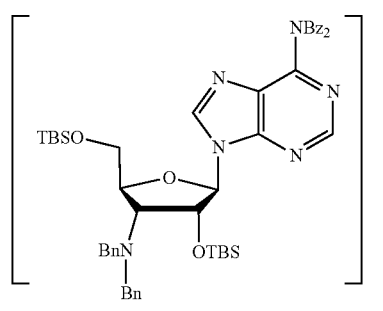

13

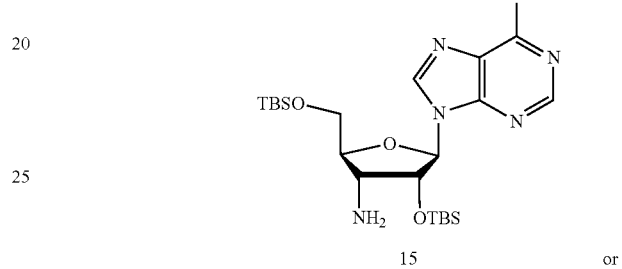

f) which is subsequently hydrogenated to afford intermediate Compound 15 or Compound 15a

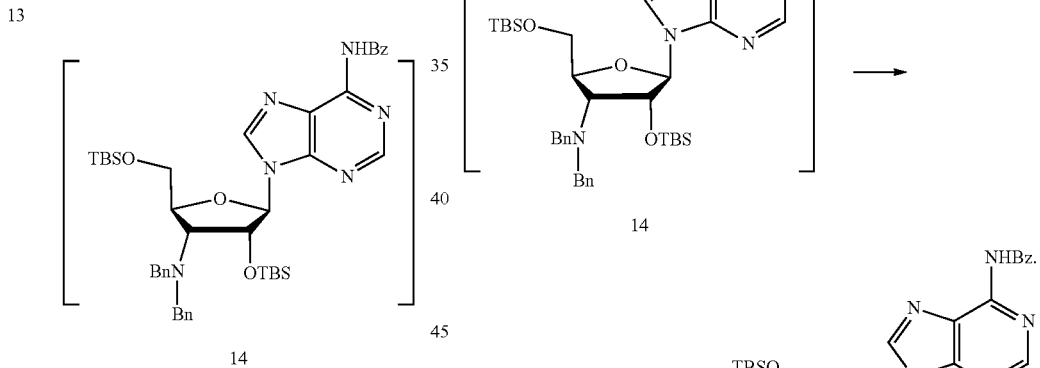

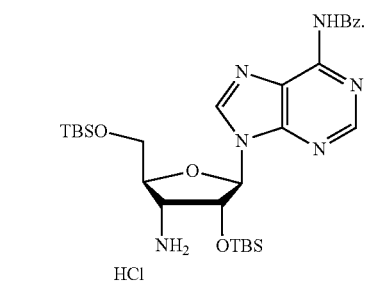

15a

10. The process according to claim 9 wherein the Vorbruggen chemistry reagent in step a) is $HA^{BZ}$.

11. The process according to claim 9 wherein the deprotecting agent in step b) is KOH.

12. The process according to claim 9 wherein the protecting group in step c) is TSCl.

13. The process according to claim 9 wherein the benzyl protecting group in step d) is BzCl.

14. The process according to claim 9 wherein the hydrogenation reagent in step f) is $PdCl_2$ or Pd/C.

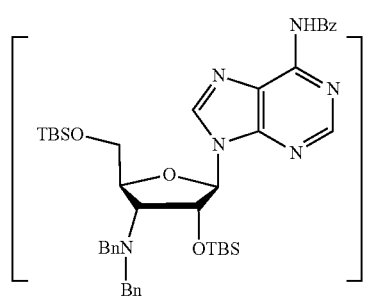

14

15. A process for preparing Compound 22 of the formula
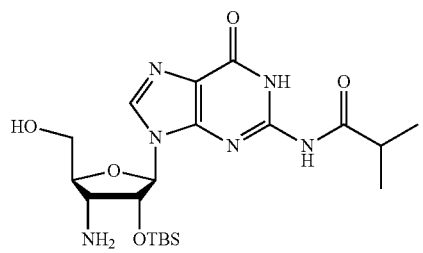
22
which comprises
a) reacting Compound 8 using Vorbrüggen chemistry to afford Compound 16 of the formula
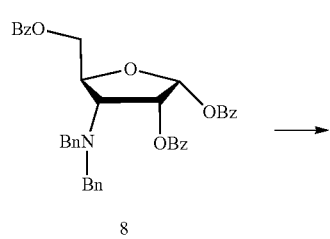
8
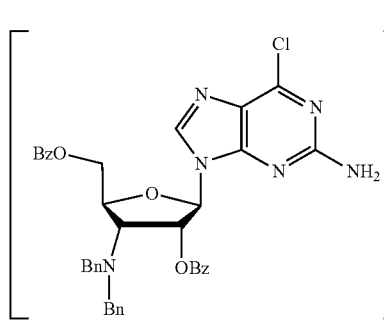
16
b) which is hydrolyzed to afford Compound 17;
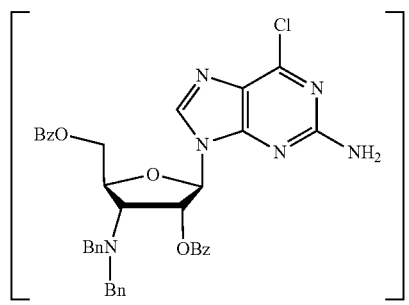
16
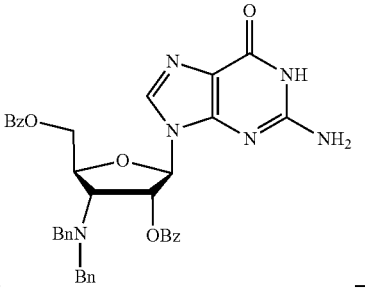
17
c) which is subsequently deprotected to afford Compound 18 of the formula
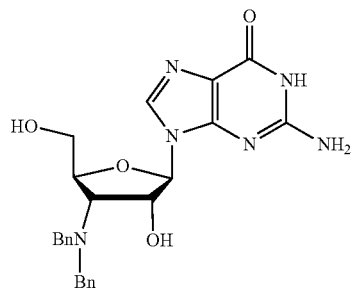
17
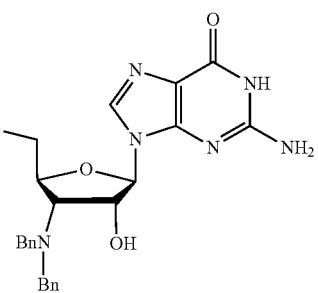
18
d) which is then protected to afford Compound 19 of the formula,
18

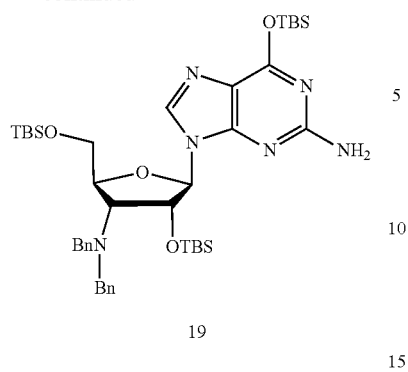
19
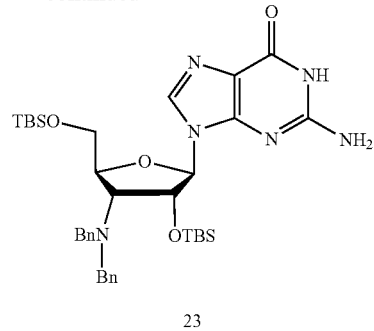
23
e) which is further protected using an isobutyryl containing reagent to afford Compound 20 of the formula,
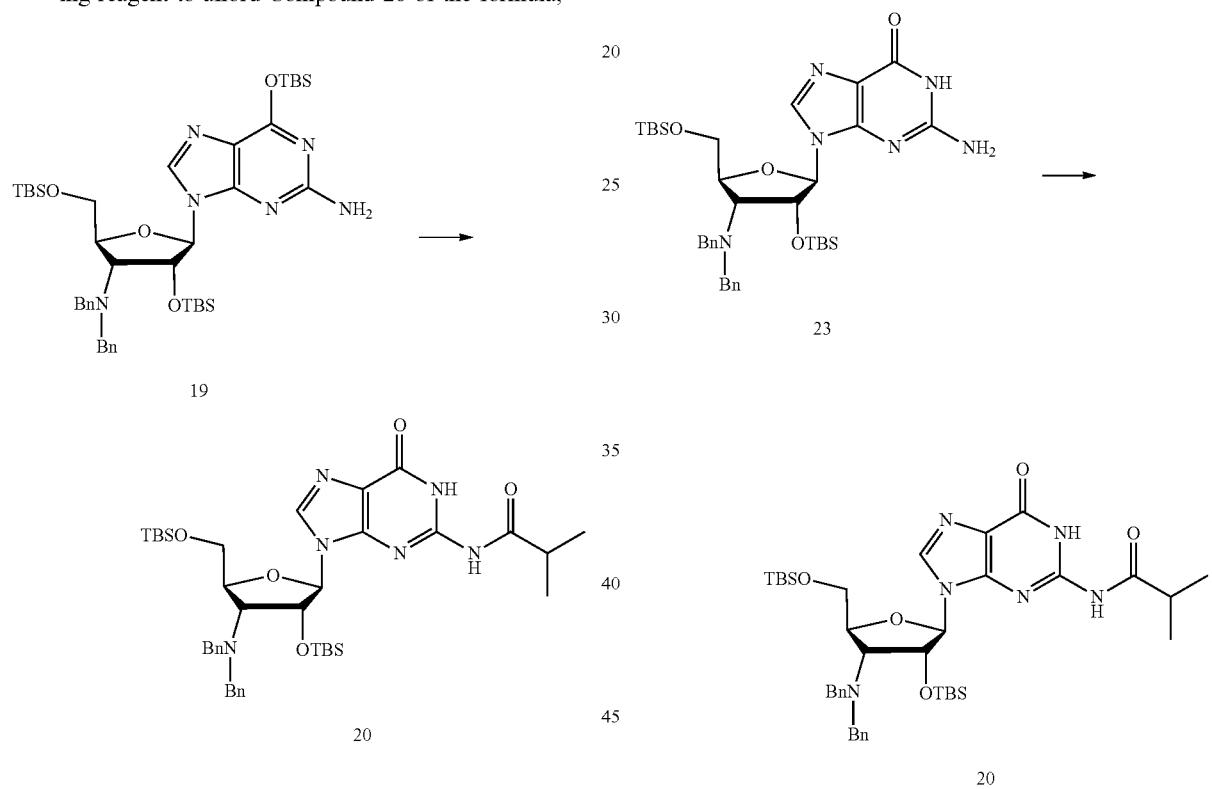
or alternatively, Compound 19 is reacted to afford Compound 23 which is further protected using an isobutyryl containing reagent to afford Compound 20
f) which is deprotected under acidic conditions to afford Compound 21 of the formula
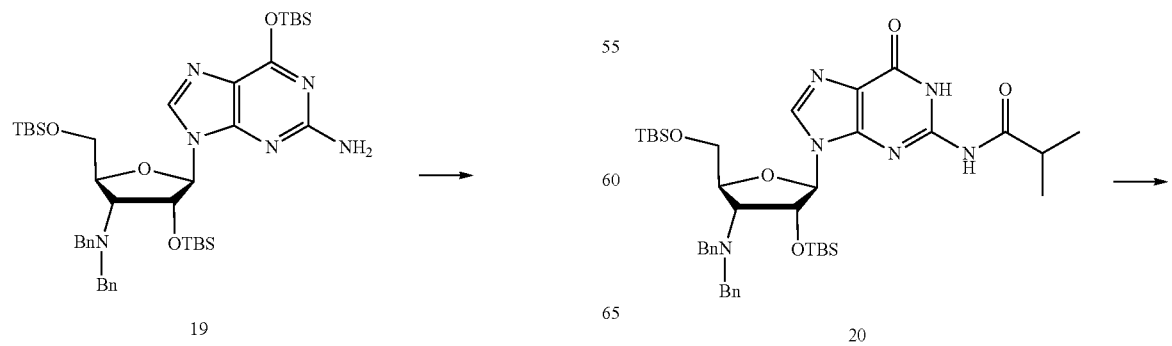

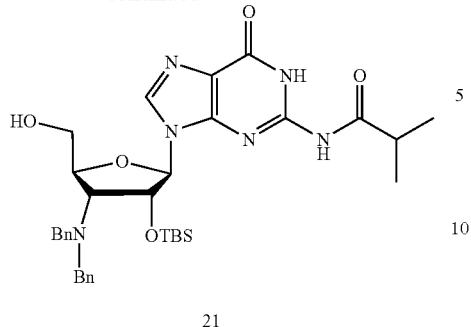

21 g) which is then hydrogenated to afford Compound 22.

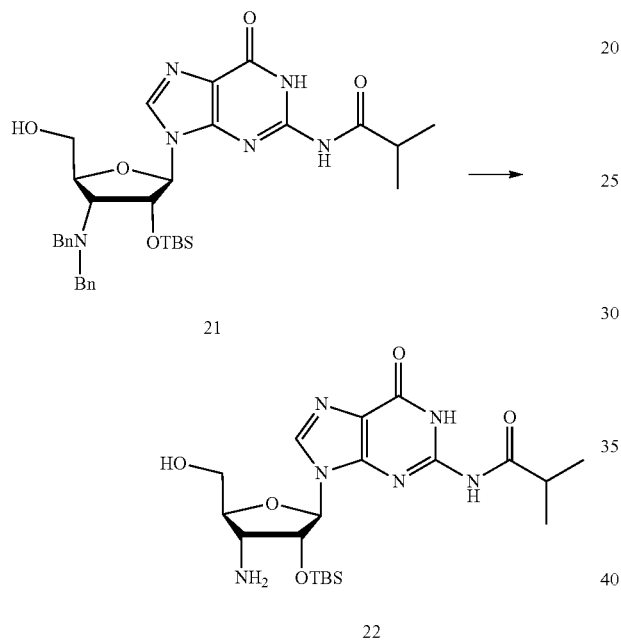

21

22

16. The process according to claim 15 wherein the Vorbruggen chemistry reagent in step a) is HG$^{CL}$.

17. The process according to claim 15 wherein the hydrolyzing agent in step b) is TsOH.

18. The process according to claim 15 wherein the deprotecting agent in step c) is KOH.

19. The process according to claim 15 wherein the protecting agent in step d) is TBSCl.

20. The process according to claim 15 wherein the isobutyl protecting group in step e) is iBuCOCl.

21. The process according to claim 15 wherein the deprotecting agent in step f) is TsOH.

22. The process according to claim 15 wherein the hydrogenation reagent in step g) is Pd/C.

23. A compound selected from the following

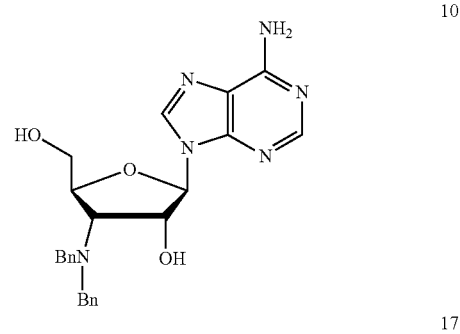

10

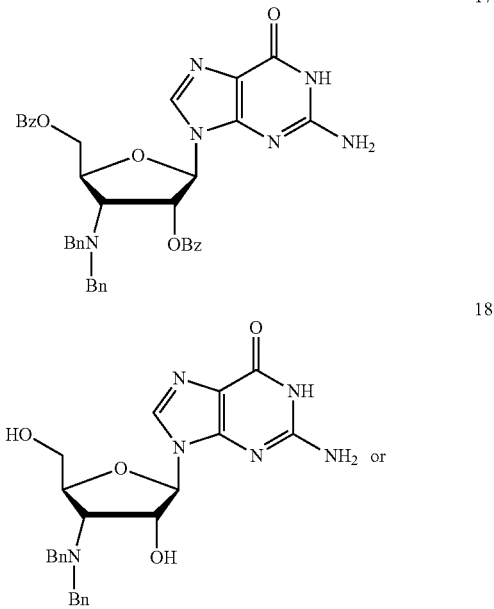

17

18 or

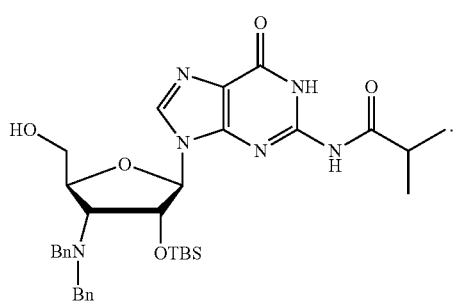

21

* * * * *

UNITED STATES PATENT AND TRADEMARK OFFICE
CERTIFICATE OF CORRECTION

PATENT NO. : 12,060,384 B2
APPLICATION NO. : 17/428548
DATED : August 13, 2024
INVENTOR(S) : Changxia Yuan et al.

Page 1 of 1

It is certified that error appears in the above-identified patent and that said Letters Patent is hereby corrected as shown below:

On the Title Page

Column 2, Line 14, Delete "Reenginecred" and insert -- Reengineered --.

In the Claims

Columns 55-56, Claim 9, Lines 52-67 (approx.), delete " 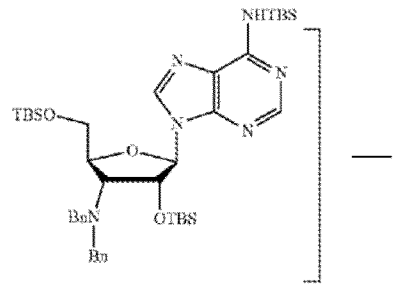 "

and insert -- 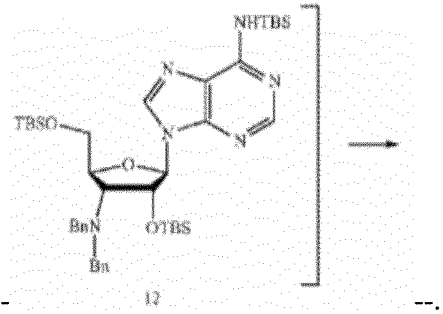 --.

Columns 58, Claim 10, Lines 56-57, delete "Vorbruggen" and insert -- Vorbrüggen --.

Columns 63, Claim 16, Lines 45-46 (approx.), delete "Vorbruggen" and insert -- Vorbrüggen --.

Signed and Sealed this
Eighteenth Day of March, 2025

Coke Morgan Stewart
*Acting Director of the United States Patent and Trademark Office*